United States Patent
Brodin et al.

(10) Patent No.: US 7,189,816 B1
(45) Date of Patent: Mar. 13, 2007

(54) COMPOUNDS

(75) Inventors: Thomas Brodin, Råå (SE); Pia J. Karlström, Lund (SE); Lennart G. Ohlsson, Lund (SE); Jesper M. Tordsson, Lund (SE); Philip P. Kearney, Lund (SE); Bo H. K. Nilson, Lund (SE)

(73) Assignee: Active Biotech AB, Lund (SE)

( * ) Notice: Subject to any disclaimer, the term of this patent is extended or adjusted under 35 U.S.C. 154(b) by 119 days.

(21) Appl. No.: 10/088,639

(22) PCT Filed: Oct. 26, 2000

(86) PCT No.: PCT/SE00/02082

§ 371 (c)(1),
(2), (4) Date: Mar. 20, 2002

(87) PCT Pub. No.: WO01/30854

PCT Pub. Date: May 3, 2001

(30) Foreign Application Priority Data

Oct. 28, 1999 (SE) .................................. 9903895

(51) Int. Cl.
C07K 16/00 (2006.01)
(52) U.S. Cl. .............................. 530/387.1; 530/387.3; 530/388.8; 530/388.85; 530/388.15; 530/391.5; 530/391.7; 424/130.1; 424/133.1; 424/156.1; 424/179.1; 424/183.1
(58) Field of Classification Search .............. 530/387.1, 530/387.3, 388.8, 388.85, 388.15, 391.5, 530/391.7; 424/130.1, 133.1, 156.1, 179.1, 424/183.1
See application file for complete search history.

(56) References Cited

U.S. PATENT DOCUMENTS

| | | | | |
|---|---|---|---|---|
| 5,320,942 | A * | 6/1994 | Quaranta et al. | 435/7.23 |
| 6,113,898 | A * | 9/2000 | Anderson et al. | 424/133.1 |
| 6,180,370 | B1 * | 1/2001 | Queen et al. | 435/69.6 |

FOREIGN PATENT DOCUMENTS

| | | |
|---|---|---|
| EP | 0 537 654 | 4/1993 |
| GB | 2305921 A | 4/1997 |
| WO | WO 94/04679 A1 | 3/1994 |
| WO | WO 99/06834 A2 | 2/1999 |

OTHER PUBLICATIONS

Fernsten et al Cancer Research 51:926-934, 1991.*
Ezzell (J. NIH Res, 1995, 7:46-49.*
Spitler (Cancer Biotherapy, 1995, 10:1-3.*
Boon (Adv Can Res, 1992, 58:177-210.*
Freshney (Culture of Animal Cells, A Manual of Basic Technique, Alan R. Liss, Inc., 1983, New York, p. 4.*
Dermer (Bio/Technology, 1994, 12:320.*
Gura (Science, 1997, 278:1041-1042.*
Rudlkoff et al (Proc Natl Acad Sci USA 1982 vol. 79 p. 1979.*
Burgess et al, Journal of Cell Biology vol. 111 Nov. 1990 2129-2138.*
Schwartz et al, Proc Natl Acad Sci USA vol. 84:6408-6411 (1987).*
Lazar et al Molecular and Cellular Biology Mar. 1988 vol. 8 No. 3 1247-1252,*
Lin et al Biochemistry USA vol. 14:1559-1563 (1975).*
Ibragimova and Eade (Biophysical Journal, Oct. 1999, vol. 77, pp. 2191-2198).*
Rudikoff et al (Proc. Natl. Acad. Sci. USA 1982 vol. 79 p. 1979).*
Colman et al (Research in Immunology 1994, 145:33-36).*
Jerome Decosse et al., "Colorectal Cancer: Detection, Treatment, and Rehabilitation." CA Cancer J. Clin, vol. 44, No. 1, Jan./Feb. 1994, pp. 27-42. American Cancer Society, Atlanta, GA.
G. Riethmüller et al., "Monoclonal Antibody Therapy for Resected Dukes' C Colorectal Cancer: Seven-Year Outcome of a Multicenter Randomized trial." *Journal of Clinical Oncology*, vol. 16, No. 5 May, 1998, pp. 1788-1794. American Society of Clinical Oncology, Alexandria, VA.
Joseph A. Kuhn et al. "Monoclonal Antibodies and Colorectal Carcinoma: A Clinical Review of Diagnostic Applications." *Cancer Investigation*, 12(3), 1994, pp. 314-323. Marcel Dekker, Inc., New York, NY.
Jesper Tordsson et al., "Efficient selection of scFv antibody phage by adsorption to in situ expressed antigens in tissue sections." *Journal of Immunological Methods*, 210 (1997), pp. 11-23. North Holland Publishing, Amsterdam, Holland.
L. Aujame et al., "High affinity human antibodies by phage display." *Human Antibodies*, 1997, vol. 8, 4, pp. 155-168. IOS Press, Amsterdam, Holland.
Robert K. Clark, et al., "Immunohistochemical Analysis of Antiserum from Rhesus Monkeys Immunized with Human Colon Carcinoma." *Cancer Research*, 49, Jul. 1, 1989, pp. 3656-3661. American Association for Cancer Research, Baltimore, MD.

(Continued)

Primary Examiner—Larry R. Helms
Assistant Examiner—Parithosh K. Tungaturthi
(74) Attorney, Agent, or Firm—Buchanan Ingersoll & Rooney PC

(57) ABSTRACT

An antibody, or a derivate or a fragment thereof, having a binding structure for a target structure is described. The antibody is displayed in, and on the cell surface of, human gastrointestinal epithelial tumour cells and in a subpopulation of normal human gastrointestinal epithelial cells. Said binding structure comprises the complementarity determining region (CDR) sequences in the light chain comprising essentially the amino acids number 23–33 (CDR1), 49–55 (CDR2), 88–98 (CDR3) of the amino acid sequence shown in SEQ ID NO:2, and the CDR sequences in the heavy chain comprising essentially the amino acids number 158–162 (CDR1), 177–193 (CDR2, 226–238 (CDR3) of the amino acid sequence shown in SEQ ID NO:2, or other binding structures with similar unique binding properties. There is also described a target structure displayed in, or on the surface of tumour cells, vaccine compositions, pharmaceutical compositions as well as methods related to human malignant diseases.

10 Claims, 10 Drawing Sheets

OTHER PUBLICATIONS

Figure 1:
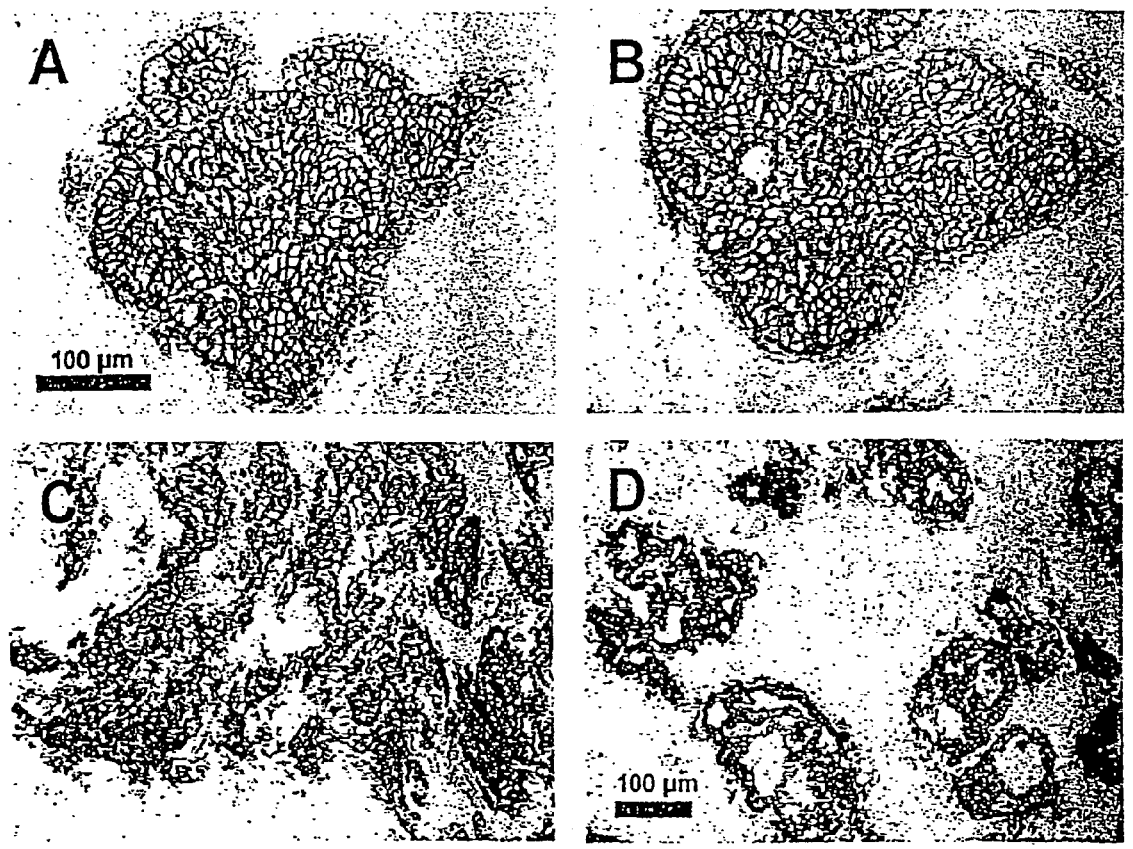

Alan P. Lewis, et al. "Cloning and Sequence Analysis of κ and γ Cynomolgus Monkey Immunoglobulin cDNAs," *Developmental and Comparative Immunology*, vol. 17, 1993, pp. 549-560. Pergamon Press Ltd., Oxford, UK.

Thomas N. Brodin et al. "Man-made superantigens: Tumor-selective agents for T-cell-based therapy." *Advanced Drug Delivery Reviews* 31 (1998) pp. 131-142). Elsevier Science B.V., Amsterdam, Holland.

Mikael Dohlsten et al., "Monoclonal antibody-superantigen fusion proteins: Tumor-specific agents for T-cell-based tumor therapy." *Proc. Natl. Acad. Sci USA*, vol. 91,, Sep. 1994, Immunology, pp. 8945-8949. National Academy of Sciences, Washington, D.C.

Changnian Liu, et al., "Eradication of large colon tumor xenografts by targeted delivery of maytansinoids," *Proc. Natl. Acad. Sci USA*, vol. 93, Aug. 1996, Medical Sciences, pp. 8618-8623, National Academy of Sciences, Washington, D.C.

Garzino-Demo et al., "Altered expression of α6 integrin subunit in oral squamous cell carcinoma and oral potentially malignant lesions", *Oral Oncology*, 34 (1998), pp. 204-210.

Hogervorst et al., "Biochemical Characterization and Tissue Distribution of the A and B Variants of the Integrin α6 Subunit", *The Journal of Cell Biology*, vol. 121, Apr. 1993, pp. 179-191.

Tennenbaum et al., "A splice variant of α6 integrin is associated with malignant conversion in mouse skin tumorigenesis", *Proc. Natl. Acad. Sci. USA*, vol. 92, Jul. 1995, pp. 7041-7045.

Weinel et al., "The α6-Integrin Receptor in Pancreatic Carcinoma", *Gastroenterology*, 1995, 108: 523-532.

Pulkkinen et al., "Novel ITGB4 Mutations in Lethal and Nonlethal Variants of Epidermolysis Bullosa with Pyloric Atresia: Missense versus Nonsense", *Am. J. Hum. Genet.*, 63: 1376-3787 (1998).

Chao et al., "A Function for the Integrin $\alpha_6\beta_4$ in the Invasive Properties of Colorectal Carcinoma Cells", *Cancer Research*, 56, 4811-4819, Oct. 15, 1996.

Rabinovitz et al., "The Integrin α6β4 and the Biology of Carcinoma", *Biochem. Cell Biol.*, 74:811-821 (1996).

Koretz et al., "Comparative evaluation of Integrin α- β-chain expression in colorectal carcinoma cell lines and in their tumors of origin", *Virchows Archiv*, (1994) 425-429—236.

Mimori et al., "Clinical significance of integrin α6 mRNA expression in gastric carcinoma", *International Journal of Oncology*, 11: 959-964, (1997).

Patriarca et al., "VLA-alpha-3 and VLA-alpha-6 integrins may lack the cytoplasmic domain in colon adenocarcinomas: An immunocytochemical and RT-PCR study", *Modern Pathology*, vol. 8, No. 1, 1995, p. 66A.

Oxford Dictionary of Biochemistry and Molecular Biology, 1997, p. 165, Oxford University Press, New York.

Dohlsten et al., "Monoclonal antibody-superantigen fusion proteins: Tumor-specific agents for T-cell based tumor therapy", Proc. Natl. Acad. Sci. USA, Sep. 1994, vol. 91, pp. 8945-8949, Pharmacia Oncology Immunology, Lund, Sweden.

* cited by examiner

FIG. 5A

TA6-Human integrin ALPHA-6A

MAAAGQLCLLYLSAGLLSRLGAAFNLDTREDNVIRKYGDPGSLFGFSLAMHWQLQP
EDKRLLLVGAPRGEALPLQRANRTGGLYSCDITARGPCTRIEFDNDADPTSESKEDQ
WMGVTVQSQGPGGKVVTCAHRYEKRQHVNTKQESRDIFGRCYVLSQNLRIEDDMD
GGDWSFCDGRLRGHEKFGSCQQGVAATFTKDFHYIVFGAPGTYNWKGIVRVEQKN
NTFFDMNIFEDGPYEVGGETEHDESLVPVPANSYLGFSLDSGKGIVSKDEITFVSGAPR
ANHSGAVVLLKRDMKSAHLLPEHIFDGEGLASSFGYDVAVVDLNKDGWQDIVIGAP
QYFDRDGEVGGAVYVYMNQQGRWNNVKPIRLNGTKDSMFGIAVKNIGDINQDGYP
DIAVGAPYDDLGKVFIYHGSANGINTKPTQVLKGISPYFGYSIAGNMDLDRNSYPDV
AVGSLSDSVTIFRSRPVINIQKTITVTPNRIDLRQKTACGAPSGICLQVKSCFEYTANPA
GYNPSISIVGTLEAEKERRKSGLSSRVQFRNQGSEPKYTQELTLKRQKQKVCMEETL
WLQDNIRDKLRPIPITASVEIQEPSSRRRVNSLPEVLPILNSDEPKTAHIDVHFLKEGCG
DDNVCNSNLKLEYKFCTREGNQDKFSYLPIQKGVPELVLKDQKDIALEITVTNSPSNP
RNPTKDGDDAHEAKLIATFPDTLTYSAYRELRAFPEKQLSCVANQNGSQADCELGNP
FKRNSNVTFYLVLSTTEVTFDTPDLDINLKLETTSNQDNLAPITAKAKVVIELLLSVSG
VAKPSQVYFGGTVVGEQAMKSEDEVGSLIEYEFRVINLGKPLTNLGTATLNIQWPKEI
SNGKWLLYLVKVESKGLEKVTCEPQKEINSLNLTESHNSRKKREITEKQIDDNRKFSL
FAERKYQTLNCSVNVNCVNIRCPLRGLDSKASLILRSRLWNSTFLEEYSKLNYLDILM
RAFIDVTAAAENIRLPNAGTQVRVTVFPSKTVAQYSGVPWWIILVAILAGILMLALLV
FILWKCGFFKRNKKDHYDATYHKAEIHAQPSDKERLTSDA

FIG. 5B

INTEGRIN BETA-4 (PRECURSOR)

MAGPRPSPWARLLLAALISVSLSGTLANRCKKAPVKSCTECVRVDKDCAYCTDEMF
RDRRCNTQAELLAAGCQRESIVVMESSFQITEETQIDTTLRRSQMSPQGLRVRLRPGE
ERHFELEVFEPLESPVDLYILMDFSNSMSDDLDNLKKMGQNLARVLSQLTSDYTIGFG
KFVDK<u>VSVPQTDMRPEKLKEPWPNSDPPFSFKNVISL</u>TEDVDEF<u>R</u>NKLQGERISGNLD
APEGGFDAILQTAVCTRDIGWRPDSTHLLVFSTESAFHYEADGANVLAGIMSRNDER
CHLDTTGTYTQYR<u>TQDYPSVPTLVRL</u>LAKHNIIPIFAVTNYSYSYYEKLHTYFPVSSLG
VLQEDSSNIVELLEEAFNRIRSNLDIRALDSPRGLRTEVTSKMFQKTRTGSFHIR<u>RGEV</u>
<u>GIYQVQLRALEHVDGTHVCQLPEDQKGNIHLKPSFSDGLKMDAGIICDVCTCELQKE</u>
VRSARCSFNGDFVCGQCVCSEGWSGQTCNCSTGSLSDIQPCLREGEDKPCSGRGECQ
CGHCVCYGEGR<u>YEGQFCEYDNFQCPR</u>TSGFLCNDRGRCSMGQCVCEPGWTGPSCDC
PLSNATCIDSNGGICNGRGHCECGRCHCHQQSLYTDTICEINYSAIHPGLCEDLR<u>SCVQ</u>
<u>CQAWGTGEKKGR</u>TCEECNFKVKMVDELKRAEEVVVRCSFR<u>DEDDDCTYSYTMEGD</u>
<u>GAPGPNSTVLVHKKK</u>DCPPGSFWWLIPLLLLLLPLLALLLLLCWKYCACCKACLALL
PCCNRGHMVGFKEDHYMLRENLMASDHLDTPMLRSGNLKGRDVVRWKVTNNMQR
PGFATHAASINPTELVPYGLSLRLARLCTENLLKPDTRECAQLR<u>QEVEENLNEVYRQ</u>I
SGVHKLQQTKFRQQPNAGKKQDHTIVDTVLMAPRSAKPALLKLTEKQVEQRAFHDL
K<u>VAPGYYTLTADQDAR</u>GMVEFQEGVELVDVR<u>VPLFIRPEDDDEKQ</u>LLVEAIDVPAG
TATLGRRLVNITIIKEQAR<u>DVVSFEQPEFSV</u>SRGDQVARIPVIRRVLDGGKSQVSYRTQ
DGTAQGNRDYIPVEGELLFQPGEAWKELQVK<u>LLELQEVDSLLR</u>GRQVRRFHVQLSNP
KFGAHLGQPHSTTIIIRDPDELDRSFTSQMLSSQPPPHGDLGAPQNPNAKAAGSRKIHF
NWLPPSGKPMGYRVKYWIQGDSESEAHLLDSKVPSVELTNLYPYCDYEMK<u>VCAYG</u>
<u>AQGEGPYSSLVSCR</u>THQEVPSEPGRLAFNVVSSTVTQLSWAEPAETNGEITAYEVCY
GLVNDDNRPIGPMKK<u>VLVDNPKNR</u>MLLIENLRESQPYRYTVKARNGAGWGPEREAII
NLATQPKRPMSIPIIPDIPIVDAQSGEDYDSFLMYSDDVLRSPSGSQRPSVSDDTGCGW
KFEPLLGEELDLRRVTWRLPPELIPRLSASSGRSSDAEAPTAPRTTAARAGRAAAVPR
SATPGPPGEHLVNGRMDFAFPGSTNSLHRMTTTSAAAYGTHLSPHVPHRVLSTSSTLT
RDYNSLTRSEHSHSTTLPRDYSTLTSVSSHGLPPIWEHGRSRLPLSWALGSRSRAQMK
GFPPSRGPRDSIILAGRPAAPSWGPDSRLTAGVPDTPTRLVFSALGPTSLRVSWQEPRC
ERPLQGYSVEYQLLNGGELHRLNIPNPAQTSVVVEDLLPNHSYVFRVRAQSQEGWGR
EREGVITIESQVHPQSPLCPLPGSAFTLSTPSAPGPLVFTALSPDSLQLSWERPRRPNGD
IVGYLVTCEMAQGGGPATAFRVDGDSPESRLTVPGLSENVPYKFKVQARTTEGFGPE
REGIITIESQDGGPFPQLGSRAGLFQHPLQSEYSSITTTHTSATEPFLVDGPTLGAQHLE
AGGSLTRHVTQEFVSRTLTTSGTLSTHMDQQFFQT (i)

FIG. 8B

SEQUENCE LISTING

```
<160> NUMBER OF SEQ ID NOS: 51

<210> SEQ ID NO 1
<211> LENGTH: 747
<212> TYPE: DNA
<213> ORGANISM: Macaca fascicularis
<220> FEATURE:
<221> NAME/KEY: CDS
<222> LOCATION: (1)..(747)
<223> OTHER INFORMATION: Coding sequence VL (1-109) - modified Huston
      linker (110-127) - VH (128-249)

<400> SEQUENCE: 1 tct tct gag ctg act cag ggc cct gca ttg tct gtg gcc ttg gga cat        48
Ser Ser Glu Leu Thr Gln Gly Pro Ala Leu Ser Val Ala Leu Gly His
 1               5                  10                  15 aca gtc agg atg acc tgc caa gga gac agc ctc aaa acc tat tat gca        96
Thr Val Arg Met Thr Cys Gln Gly Asp Ser Leu Lys Thr Tyr Tyr Ala
             20                  25                  30 agc tgg tac cag cag aag cca ggc cag gtc cct gtg ctg gtc atc tat       144
Ser Trp Tyr Gln Gln Lys Pro Gly Gln Val Pro Val Leu Val Ile Tyr
         35                  40                  45 ggt aac aac tac cgg ccc tca ggg atc cca ggc cga ttc tct ggc tcc       192
Gly Asn Asn Tyr Arg Pro Ser Gly Ile Pro Gly Arg Phe Ser Gly Ser
     50                  55                  60 tgg tca gga aac aca gct tcc ttg acc atc act gcg gct cag gtg gaa       240
Trp Ser Gly Asn Thr Ala Ser Leu Thr Ile Thr Ala Ala Gln Val Glu
 65                  70                  75                  80 gat gag gct gac tat tac tgt aac tcc tgg gac agc agc ggt acc cat       288
Asp Glu Ala Asp Tyr Tyr Cys Asn Ser Trp Asp Ser Ser Gly Thr His
                 85                  90                  95 ccg gta ttc ggc gga ggg acc cgg gtg acc gtc cta ggt caa gcc aac       336
Pro Val Phe Gly Gly Gly Thr Arg Val Thr Val Leu Gly Gln Ala Asn
            100                 105                 110 ggt gaa ggc ggc tct ggt ggc ggg gga tcc gga ggc ggc ggt tct gag       384
Gly Glu Gly Gly Ser Gly Gly Gly Gly Ser Gly Gly Gly Gly Ser Glu
        115                 120                 125
```

```
gtg cag ttg gtg gag tct ggg gga ggc ttg gta aag cct ggg ggg tcc      432
Val Gln Leu Val Glu Ser Gly Gly Gly Leu Val Lys Pro Gly Gly Ser
    130                 135                 140 ctg aga ctc tct tgt gta gcc tct ggg tcc atc ttc agt agc tct gtt      480
Leu Arg Leu Ser Cys Val Ala Ser Gly Ser Ile Phe Ser Ser Ser Val
145                 150                 155                 160 atg cac tgg gtc cgc cag gct cca gga aag ggt ctg gag tgg gtc tca      528
Met His Trp Val Arg Gln Ala Pro Gly Lys Gly Leu Glu Trp Val Ser
                165                 170                 175 gtt att agt gaa aat ggg cgt acc att aac tac gca gac tct gtg aag      576
Val Ile Ser Glu Asn Gly Arg Thr Ile Asn Tyr Ala Asp Ser Val Lys
            180                 185                 190 ggc cga ttc acc atc tcc aga gac aac gcc aag aac tca ctg ttt ctg      624
Gly Arg Phe Thr Ile Ser Arg Asp Asn Ala Lys Asn Ser Leu Phe Leu
        195                 200                 205 cag atg aac agc ctg aca ggc gag gac acg gcc gtc tat tac tgt agt      672
Gln Met Asn Ser Leu Thr Gly Glu Asp Thr Ala Val Tyr Tyr Cys Ser
    210                 215                 220 aga gag ggg gga cct gga aca acg tcc aac cgg ctc gat gcc tgg ggc      720
Arg Glu Gly Gly Pro Gly Thr Thr Ser Asn Arg Leu Asp Ala Trp Gly
225                 230                 235                 240 ccg gga gtc ctg gtc acc gtt tcc tca                                  747
Pro Gly Val Leu Val Thr Val Ser Ser
                245

<210> SEQ ID NO 2
<211> LENGTH: 249
<212> TYPE: PRT
<213> ORGANISM: Macaca fascicularis
<220> FEATURE:
<223> OTHER INFORMATION: Coding sequence VL (1-109) - modified Huston
      linker (110-127) - VH (128-249)

<400> SEQUENCE: 2

Ser Ser Glu Leu Thr Gln Gly Pro Ala Leu Ser Val Ala Leu Gly His
1               5                   10                  15

Thr Val Arg Met Thr Cys Gln Gly Asp Ser Leu Lys Thr Tyr Tyr Ala
            20                  25                  30

Ser Trp Tyr Gln Gln Lys Pro Gly Gln Val Pro Val Leu Val Ile Tyr
        35                  40                  45

Gly Asn Asn Tyr Arg Pro Ser Gly Ile Pro Gly Arg Phe Ser Gly Ser
    50                  55                  60

Trp Ser Gly Asn Thr Ala Ser Leu Thr Ile Thr Ala Ala Gln Val Glu
65                  70                  75                  80

Asp Glu Ala Asp Tyr Tyr Cys Asn Ser Trp Asp Ser Ser Gly Thr His
                85                  90                  95

Pro Val Phe Gly Gly Thr Arg Val Thr Val Leu Gly Gln Ala Asn
                100                 105                 110

Gly Glu Gly Gly Ser Gly Gly Gly Ser Gly Gly Gly Ser Glu
            115                 120                 125

Val Gln Leu Val Glu Ser Gly Gly Gly Leu Val Lys Pro Gly Gly Ser
    130                 135                 140

Leu Arg Leu Ser Cys Val Ala Ser Gly Ser Ile Phe Ser Ser Ser Val
145                 150                 155                 160

Met His Trp Val Arg Gln Ala Pro Gly Lys Gly Leu Glu Trp Val Ser
                165                 170                 175

Val Ile Ser Glu Asn Gly Arg Thr Ile Asn Tyr Ala Asp Ser Val Lys
            180                 185                 190
```

```
Gly Arg Phe Thr Ile Ser Arg Asp Asn Ala Lys Asn Ser Leu Phe Leu
            195                 200                 205

Gln Met Asn Ser Leu Thr Gly Glu Asp Thr Ala Val Tyr Tyr Cys Ser
        210                 215                 220

Arg Glu Gly Gly Pro Gly Thr Thr Ser Asn Arg Leu Asp Ala Trp Gly
225                 230                 235                 240

Pro Gly Val Leu Val Thr Val Ser Ser
                245
```

<210> SEQ ID NO 3
<211> LENGTH: 1073
<212> TYPE: PRT
<213> ORGANISM: Human
<220> FEATURE:
<223> OTHER INFORMATION: TA6-Human integrin alpha-6A

<400> SEQUENCE: 3

```
Met Ala Ala Gly Gln Leu Cys Leu Tyr Leu Ser Ala Gly Leu
 1               5                  10                  15

Leu Ser Arg Leu Gly Ala Ala Phe Asn Leu Asp Thr Arg Glu Asp Asn
            20                  25                  30

Val Ile Arg Lys Tyr Gly Asp Pro Gly Ser Leu Phe Gly Phe Ser Leu
        35                  40                  45

Ala Met His Trp Gln Leu Gln Pro Glu Asp Lys Arg Leu Leu Leu Val
    50                  55                  60

Gly Ala Pro Arg Gly Glu Ala Leu Pro Leu Gln Arg Ala Asn Arg Thr
65                  70                  75                  80

Gly Gly Leu Tyr Ser Cys Asp Ile Thr Ala Arg Gly Pro Cys Thr Arg
                85                  90                  95

Ile Glu Phe Asp Asn Asp Ala Asp Pro Thr Ser Glu Ser Lys Glu Asp
            100                 105                 110

Gln Trp Met Gly Val Thr Val Gln Ser Gln Gly Pro Gly Gly Lys Val
        115                 120                 125

Val Thr Cys Ala His Arg Tyr Glu Lys Arg Gln His Val Asn Thr Lys
    130                 135                 140

Gln Glu Ser Arg Asp Ile Phe Gly Arg Cys Tyr Val Leu Ser Gln Asn
145                 150                 155                 160

Leu Arg Ile Glu Asp Asp Met Asp Gly Gly Asp Trp Ser Phe Cys Asp
                165                 170                 175

Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
        195                 200                 205

Gly Thr Tyr Asn Trp Lys Gly Ile Val Arg Val Glu Gln Lys Asn Asn
    210                 215                 220

Thr Phe Phe Asp Met Asn Ile Phe Glu Asp Gly Pro Tyr Glu Val Gly
225                 230                 235                 240

Gly Glu Thr Glu His Asp Glu Ser Leu Val Pro Val Pro Ala Asn Ser
                245                 250                 255

Tyr Leu Gly Phe Ser Leu Asp Ser Gly Lys Gly Ile Val Ser Lys Asp
            260                 265                 270

Glu Ile Thr Phe Val Ser Gly Ala Pro Arg Ala Asn His Ser Gly Ala
        275                 280                 285

Val Val Leu Leu Lys Arg Asp Met Lys Ser Ala His Leu Leu Pro Glu
    290                 295                 300
```

-continued

```
His Ile Phe Asp Gly Glu Gly Leu Ala Ser Ser Phe Gly Tyr Asp Val
305                 310                 315                 320

Ala Val Val Asp Leu Asn Lys Asp Gly Trp Gln Asp Ile Val Ile Gly
            325                 330                 335

Ala Pro Gln Tyr Phe Asp Arg Asp Gly Glu Val Gly Gly Ala Val Tyr
        340                 345                 350

Val Tyr Met Asn Gln Gln Gly Arg Trp Asn Asn Val Lys Pro Ile Arg
    355                 360                 365

Leu Asn Gly Thr Lys Asp Ser Met Phe Gly Ile Ala Val Lys Asn Ile
    370                 375                 380

Gly Asp Ile Asn Gln Asp Gly Tyr Pro Asp Ile Ala Val Gly Ala Pro
385                 390                 395                 400

Tyr Asp Asp Leu Gly Lys Val Phe Ile Tyr His Gly Ser Ala Asn Gly
            405                 410                 415

Ile Asn Thr Lys Pro Thr Gln Val Leu Lys Gly Ile Ser Pro Tyr Phe
        420                 425                 430

Gly Tyr Ser Ile Ala Gly Asn Met Asp Leu Asp Arg Asn Ser Tyr Pro
    435                 440                 445

Asp Val Ala Val Gly Ser Leu Ser Asp Ser Val Thr Ile Phe Arg Ser
    450                 455                 460

Arg Pro Val Ile Asn Ile Gln Lys Thr Ile Thr Val Thr Pro Asn Arg
465                 470                 475                 480

Ile Asp Leu Arg Gln Lys Thr Ala Cys Gly Ala Pro Ser Gly Ile Cys
            485                 490                 495

Leu Gln Val Lys Ser Cys Phe Glu Tyr Thr Ala Asn Pro Ala Gly Tyr
        500                 505                 510

Asn Pro Ser Ile Ser Ile Val Gly Thr Leu Glu Ala Glu Lys Glu Arg
    515                 520                 525

Arg Lys Ser Gly Leu Ser Ser Arg Val Gln Phe Arg Asn Gln Gly Ser
    530                 535                 540

Glu Pro Lys Tyr Thr Gln Glu Leu Thr Leu Lys Arg Gln Lys Gln Lys
545                 550                 555                 560

Val Cys Met Glu Glu Thr Leu Trp Leu Gln Asp Asn Ile Arg Asp Lys
            565                 570                 575

Leu Arg Pro Ile Pro Ile Thr Ala Ser Val Glu Ile Gln Glu Pro Ser
        580                 585                 590

Ser Arg Arg Arg Val Asn Ser Leu Pro Glu Val Leu Pro Ile Leu Asn
    595                 600                 605

Ser Asp Glu Pro Lys Thr Ala His Ile Asp Val His Phe Leu Lys Glu
    610                 615                 620

Gly Cys Gly Asp Asp Asn Val Cys Asn Ser Asn Leu Lys Leu Glu Tyr
625                 630                 635                 640

Lys Phe Cys Thr Arg Glu Gly Asn Gln Asp Lys Phe Ser Tyr Leu Pro
            645                 650                 655

Ile Gln Lys Gly Val Pro Glu Leu Val Leu Lys Asp Gln Lys Asp Ile
        660                 665                 670

Ala Leu Glu Ile Thr Val Thr Asn Ser Pro Ser Asn Pro Arg Asn Pro
    675                 680                 685

Thr Lys Asp Gly Asp Ala His Glu Ala Lys Leu Ile Ala Thr Phe
    690                 695                 700

Pro Asp Thr Leu Thr Tyr Ser Ala Tyr Arg Glu Leu Arg Ala Phe Pro
705                 710                 715                 720

Glu Lys Gln Leu Ser Cys Val Ala Asn Gln Asn Gly Ser Gln Ala Asp
```

```
                      725                 730                 735
Cys Glu Leu Gly Asn Pro Phe Lys Arg Asn Ser Asn Val Thr Phe Tyr
            740                 745                 750
Leu Val Leu Ser Thr Thr Glu Val Thr Phe Asp Thr Pro Asp Leu Asp
            755                 760                 765
Ile Asn Leu Lys Leu Glu Thr Thr Ser Asn Gln Asp Asn Leu Ala Pro
            770                 775                 780
Ile Thr Ala Lys Ala Lys Val Val Ile Glu Leu Leu Ser Val Ser
785                 790                 795                 800
Gly Val Ala Lys Pro Ser Gln Val Tyr Phe Gly Gly Thr Val Val Gly
                    805                 810                 815
Glu Gln Ala Met Lys Ser Glu Asp Glu Val Gly Ser Leu Ile Glu Tyr
            820                 825                 830
Glu Phe Arg Val Ile Asn Leu Gly Lys Pro Leu Thr Asn Leu Gly Thr
            835                 840                 845
Ala Thr Leu Asn Ile Gln Trp Pro Lys Glu Ile Ser Asn Gly Lys Trp
            850                 855                 860
Leu Leu Tyr Leu Val Lys Val Glu Ser Lys Gly Leu Glu Lys Val Thr
865                 870                 875                 880
Cys Glu Pro Gln Lys Glu Ile Asn Ser Leu Asn Leu Thr Glu Ser His
                    885                 890                 895
Asn Ser Arg Lys Lys Arg Glu Ile Thr Glu Lys Gln Ile Asp Asp Asn
                    900                 905                 910
Arg Lys Phe Ser Leu Phe Ala Glu Arg Lys Tyr Gln Thr Leu Asn Cys
            915                 920                 925
Ser Val Asn Val Asn Cys Val Asn Ile Arg Cys Pro Leu Arg Gly Leu
            930                 935                 940
Asp Ser Lys Ala Ser Leu Ile Leu Arg Ser Arg Leu Trp Asn Ser Thr
945                 950                 955                 960
Phe Leu Glu Glu Tyr Ser Lys Leu Asn Tyr Leu Asp Ile Leu Met Arg
                    965                 970                 975
Ala Phe Ile Asp Val Thr Ala Ala Ala Glu Asn Ile Arg Leu Pro Asn
            980                 985                 990
Ala Gly Thr Gln Val Arg Val Thr Val Phe Pro Ser Lys Thr Val Ala
            995                 1000                1005
Gln Tyr Ser Gly Val Pro Trp Trp Ile Ile Leu Val Ala Ile Leu Ala
    1010                1015                1020
Gly Ile Leu Met Leu Ala Leu Leu Val Phe Ile Leu Trp Lys Cys Gly
1025                1030                1035                1040
Phe Phe Lys Arg Asn Lys Lys Asp His Tyr Asp Ala Thr Tyr His Lys
                    1045                1050                1055
Ala Glu Ile His Ala Gln Pro Ser Asp Lys Glu Arg Leu Thr Ser Asp
            1060                1065                1070
Ala
```

<210> SEQ ID NO 4
<211> LENGTH: 1875
<212> TYPE: PRT
<213> ORGANISM: Human
<220> FEATURE:
<223> OTHER INFORMATION: Integrin beta-4 precursor

<400> SEQUENCE: 4

```
Met Ala Gly Pro Arg Pro Ser Pro Trp Ala Arg Leu Leu Leu Ala Ala
1               5                   10                  15
```

-continued

```
Leu Ile Ser Val Ser Leu Ser Gly Thr Leu Ala Asn Arg Cys Lys Lys
             20                  25                  30

Ala Pro Val Lys Ser Cys Thr Glu Cys Val Arg Val Asp Lys Asp Cys
         35                  40                  45

Ala Tyr Cys Thr Asp Glu Met Phe Arg Asp Arg Arg Cys Asn Thr Gln
     50                  55                  60

Ala Glu Leu Leu Ala Ala Gly Cys Gln Arg Glu Ser Ile Val Val Met
 65                  70                  75                  80

Glu Ser Ser Phe Gln Ile Thr Glu Glu Thr Gln Ile Asp Thr Thr Leu
                 85                  90                  95

Arg Arg Ser Gln Met Ser Pro Gln Gly Leu Arg Val Arg Leu Arg Pro
            100                 105                 110

Gly Glu Glu Arg His Phe Glu Leu Glu Val Phe Glu Pro Leu Glu Ser
            115                 120                 125

Pro Val Asp Leu Tyr Ile Leu Met Asp Phe Ser Asn Ser Met Ser Asp
        130                 135                 140

Asp Leu Asp Asn Leu Lys Lys Met Gly Gln Asn Leu Ala Arg Val Leu
145                 150                 155                 160

Ser Gln Leu Thr Ser Asp Tyr Thr Ile Gly Phe Gly Lys Phe Val Asp
                165                 170                 175

Lys Val Ser Val Pro Gln Thr Asp Met Arg Pro Glu Lys Leu Lys Glu
            180                 185                 190

Pro Trp Pro Asn Ser Asp Pro Pro Phe Ser Phe Lys Asn Val Ile Ser
        195                 200                 205

Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
            260                 265                 270

Gly Ala Asn Val Leu Ala Gly Ile Met Ser Arg Asn Asp Glu Arg Cys
        275                 280                 285

His Leu Asp Thr Thr Gly Thr Tyr Thr Gln Tyr Arg Thr Gln Asp Tyr
    290                 295                 300

Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Tyr Glu Lys Leu
                325                 330                 335

His Thr Tyr Phe Pro Val Ser Ser Leu Gly Val Leu Gln Glu Asp Ser
            340                 345                 350

Ser Asn Ile Val Glu Leu Leu Glu Glu Ala Phe Asn Arg Ile Arg Ser
        355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu
                405                 410                 415

His Val Asp Gly Thr His Val Cys Gln Leu Pro Glu Asp Gln Lys Gly
            420                 425                 430
```

```
Asn Ile His Leu Lys Pro Ser Phe Ser Asp Gly Leu Lys Met Asp Ala
        435                 440                 445
Gly Ile Ile Cys Asp Val Cys Thr Cys Glu Leu Gln Lys Glu Val Arg
        450                 455                 460
Ser Ala Arg Cys Ser Phe Asn Gly Asp Phe Val Cys Gly Gln Cys Val
465                 470                 475                 480
Cys Ser Glu Gly Trp Ser Gly Gln Thr Cys Asn Cys Ser Thr Gly Ser
                    485                 490                 495
Leu Ser Asp Ile Gln Pro Cys Leu Arg Glu Gly Glu Asp Lys Pro Cys
                500                 505                 510
Ser Gly Arg Gly Glu Cys Gln Cys Gly His Cys Val Cys Tyr Gly Glu
            515                 520                 525
Gly Arg Tyr Glu Gly Gln Phe Cys Glu Tyr Asp Asn Phe Gln Cys Pro
        530                 535                 540
Arg Thr Ser Gly Phe Leu Cys Asn Asp Arg Gly Arg Cys Ser Met Gly
545                 550                 555                 560
Gln Cys Val Cys Glu Pro Gly Trp Thr Gly Pro Ser Cys Asp Cys Pro
                565                 570                 575
Leu Ser Asn Ala Thr Cys Ile Asp Ser Asn Gly Gly Ile Cys Asn Gly
                580                 585                 590
Arg Gly His Cys Glu Cys Gly Arg Cys His Cys His Gln Gln Ser Leu
            595                 600                 605
Tyr Thr Asp Thr Ile Cys Glu Ile Asn Tyr Ser Ala Ile His Pro Gly
        610                 615                 620
Leu Cys Glu Asp Leu Arg Ser Cys Val Gln Cys Gln Ala Trp Gly Thr
625                 630                 635                 640
Gly Glu Lys Lys Gly Arg Thr Cys Glu Glu Cys Asn Phe Lys Val Lys
                645                 650                 655
Met Val Asp Glu Leu Lys Arg Ala Glu Glu Val Val Val Arg Cys Ser
                660                 665                 670
Phe Arg Asp Glu Asp Asp Asp Cys Thr Tyr Ser Tyr Thr Met Glu Gly
            675                 680                 685
Asp Gly Ala Pro Gly Pro Asn Ser Thr Val Leu Val His Lys Lys Lys
        690                 695                 700
Asp Cys Pro Pro Gly Ser Phe Trp Trp Leu Ile Pro Leu Leu Leu Leu
705                 710                 715                 720
Leu Leu Pro Leu Leu Ala Leu Leu Leu Leu Cys Trp Lys Tyr Cys
                725                 730                 735
Ala Cys Cys Lys Ala Cys Leu Ala Leu Leu Pro Cys Cys Asn Arg Gly
                740                 745                 750
His Met Val Gly Phe Lys Glu Asp His Tyr Met Leu Arg Glu Asn Leu
            755                 760                 765
Met Ala Ser Asp His Leu Asp Thr Pro Met Leu Arg Ser Gly Asn Leu
        770                 775                 780
Lys Gly Arg Asp Val Val Arg Trp Lys Val Thr Asn Asn Met Gln Arg
785                 790                 795                 800
Pro Gly Phe Ala Thr His Ala Ala Ser Ile Asn Pro Thr Glu Leu Val
                805                 810                 815
Pro Tyr Gly Leu Ser Leu Arg Leu Ala Arg Leu Cys Thr Glu Asn Leu
                820                 825                 830
Leu Lys Pro Asp Thr Arg Glu Cys Ala Gln Leu Arg Gln Glu Val Glu
            835                 840                 845
Glu Asn Leu Asn Glu Val Tyr Arg Gln Ile Ser Gly Val His Lys Leu
```

-continued

```
                850                 855                 860
Gln Gln Thr Lys Phe Arg Gln Pro Asn Ala Gly Lys Lys Gln Asp
865                 870                 875                 880

His Thr Ile Val Asp Thr Val Leu Met Ala Pro Arg Ser Ala Lys Pro
                        885                 890                 895

Ala Leu Leu Lys Leu Thr Glu Lys Gln Val Glu Gln Arg Ala Phe His
            900                 905                 910

Asp Leu Lys Val Ala Pro Gly Tyr Tyr Thr Leu Thr Ala Asp Gln Asp
            915                 920                 925

Ala Arg Gly Met Val Glu Phe Gln Glu Gly Val Glu Leu Val Asp Val
        930                 935                 940

Arg Val Pro Leu Phe Ile Arg Pro Glu Asp Asp Glu Lys Gln Leu
945                 950                 955                 960

Leu Val Glu Ala Ile Asp Val Pro Ala Gly Thr Ala Thr Leu Gly Arg
                965                 970                 975

Arg Leu Val Asn Ile Thr Ile Ile Lys Glu Gln Ala Arg Asp Val Val
            980                 985                 990

Ser Phe Glu Gln Pro Glu Phe Ser Val Ser Arg Gly Asp Gln Val Ala
        995                 1000                1005

Arg Ile Pro Val Ile Arg Arg Val Leu Asp Gly Gly Lys Ser Gln Val
    1010                1015                1020

Ser Tyr Arg Thr Gln Asp Gly Thr Ala Gln Gly Asn Arg Asp Tyr Ile
1025                1030                1035                1040

Pro Val Glu Gly Glu Leu Leu Phe Gln Pro Gly Glu Ala Trp Lys Glu
            1045                1050                1055

Leu Gln Val Lys Leu Leu Glu Leu Gln Glu Val Asp Ser Leu Leu Arg
        1060                1065                1070

Gly Arg Gln Val Arg Arg Phe His Val Gln Leu Ser Asn Pro Lys Phe
    1075                1080                1085

Gly Ala His Leu Gly Gln Pro His Ser Thr Thr Ile Ile Ile Arg Asp
    1090                1095                1100

Pro Asp Glu Leu Asp Arg Ser Phe Thr Ser Gln Met Leu Ser Ser Gln
1105                1110                1115                1120

Pro Pro His Gly Asp Leu Gly Ala Pro Gln Asn Pro Asn Ala Lys
            1125                1130                1135

Ala Ala Gly Ser Arg Lys Ile His Phe Asn Trp Leu Pro Pro Ser Gly
        1140                1145                1150

Lys Pro Met Gly Tyr Arg Val Lys Tyr Trp Ile Gln Gly Asp Ser Glu
    1155                1160                1165

Ser Glu Ala His Leu Leu Asp Ser Lys Val Pro Ser Val Glu Leu Thr
1170                1175                1180

Asn Leu Tyr Pro Tyr Cys Asp Tyr Glu Met Lys Val Cys Ala Tyr Gly
1185                1190                1195                1200

Ala Gln Gly Glu Gly Pro Tyr Ser Ser Leu Val Ser Cys Arg Thr His
        1205                1210                1215

Gln Glu Val Pro Ser Glu Pro Gly Arg Leu Ala Phe Asn Val Val Ser
            1220                1225                1230

Ser Thr Val Thr Gln Leu Ser Trp Ala Glu Pro Ala Glu Thr Asn Gly
        1235                1240                1245

Glu Ile Thr Ala Tyr Glu Val Cys Tyr Gly Leu Val Asn Asp Asp Asn
    1250                1255                1260

Arg Pro Ile Gly Pro Met Lys Lys Val Leu Val Asp Asn Pro Lys Asn
1265                1270                1275                1280
```

-continued

```
Arg Met Leu Leu Ile Glu Asn Leu Arg Glu Ser Gln Pro Tyr Arg Tyr
            1285                1290                1295

Thr Val Lys Ala Arg Asn Gly Ala Gly Trp Gly Pro Glu Arg Glu Ala
        1300                1305                1310

Ile Ile Asn Leu Ala Thr Gln Pro Lys Arg Pro Met Ser Ile Pro Ile
        1315                1320                1325

Ile Pro Asp Ile Pro Ile Val Asp Ala Gln Ser Gly Glu Asp Tyr Asp
    1330                1335                1340

Ser Phe Leu Met Tyr Ser Asp Asp Val Leu Arg Ser Pro Ser Gly Ser
1345                1350                1355                1360

Gln Arg Pro Ser Val Ser Asp Asp Thr Gly Cys Gly Trp Lys Phe Glu
            1365                1370                1375

Pro Leu Leu Gly Glu Glu Leu Asp Leu Arg Arg Val Thr Trp Arg Leu
            1380                1385                1390

Pro Pro Glu Leu Ile Pro Arg Leu Ser Ala Ser Ser Gly Arg Ser Ser
        1395                1400                1405

Asp Ala Glu Ala Pro Thr Ala Pro Arg Thr Thr Ala Ala Arg Ala Gly
    1410                1415                1420

Arg Ala Ala Val Pro Arg Ser Ala Thr Pro Gly Pro Pro Gly Glu
1425                1430                1435                1440

His Leu Val Asn Gly Arg Met Asp Phe Ala Phe Pro Gly Ser Thr Asn
            1445                1450                1455

Ser Leu His Arg Met Thr Thr Thr Ser Ala Ala Ala Tyr Gly Thr His
            1460                1465                1470

Leu Ser Pro His Val Pro His Arg Val Leu Ser Thr Ser Thr Leu
        1475                1480                1485

Thr Arg Asp Tyr Asn Ser Leu Thr Arg Ser Glu His Ser His Ser Thr
    1490                1495                1500

Thr Leu Pro Arg Asp Tyr Ser Thr Leu Thr Ser Val Ser Ser His Gly
1505                1510                1515                1520

Leu Pro Pro Ile Trp Glu His Gly Arg Ser Arg Leu Pro Leu Ser Trp
            1525                1530                1535

Ala Leu Gly Ser Arg Ser Arg Ala Gln Met Lys Gly Phe Pro Pro Ser
            1540                1545                1550

Arg Gly Pro Arg Asp Ser Ile Ile Leu Ala Gly Arg Pro Ala Ala Pro
        1555                1560                1565

Ser Trp Gly Pro Asp Ser Arg Leu Thr Ala Gly Val Pro Asp Thr Pro
    1570                1575                1580

Thr Arg Leu Val Phe Ser Ala Leu Gly Pro Thr Ser Leu Arg Val Ser
1585                1590                1595                1600

Trp Gln Glu Pro Arg Cys Glu Arg Pro Leu Gln Gly Tyr Ser Val Glu
            1605                1610                1615

Tyr Gln Leu Leu Asn Gly Gly Glu Leu His Arg Leu Asn Ile Pro Asn
            1620                1625                1630

Pro Ala Gln Thr Ser Val Val Val Glu Asp Leu Leu Pro Asn His Ser
        1635                1640                1645

Tyr Val Phe Arg Val Arg Ala Gln Ser Gln Glu Gly Trp Gly Arg Glu
    1650                1655                1660

Arg Glu Gly Val Ile Thr Ile Glu Ser Gln Val His Pro Gln Ser Pro
1665                1670                1675                1680

Leu Cys Pro Leu Pro Gly Ser Ala Phe Thr Leu Ser Thr Pro Ser Ala
            1685                1690                1695
```

-continued

```
Pro Gly Pro Leu Val Phe Thr Ala Leu Ser Pro Asp Ser Leu Gln Leu
        1700                1705                1710

Ser Trp Glu Arg Pro Arg Arg Pro Asn Gly Asp Ile Val Gly Tyr Leu
    1715                1720                1725

Val Thr Cys Glu Met Ala Gln Gly Gly Pro Ala Thr Ala Phe Arg
1730                1735                1740

Val Asp Gly Asp Ser Pro Glu Ser Arg Leu Thr Val Pro Gly Leu Ser
1745                1750                1755                1760

Glu Asn Val Pro Tyr Lys Phe Lys Val Gln Ala Arg Thr Thr Glu Gly
                1765                1770                1775

Phe Gly Pro Glu Arg Glu Gly Ile Ile Thr Ile Glu Ser Gln Asp Gly
        1780                1785                1790

Gly Pro Phe Pro Gln Leu Gly Ser Arg Ala Gly Leu Phe Gln His Pro
    1795                1800                1805

Leu Gln Ser Glu Tyr Ser Ser Ile Thr Thr Thr His Thr Ser Ala Thr
1810                1815                1820

Glu Pro Phe Leu Val Asp Gly Pro Thr Leu Gly Ala Gln His Leu Glu
1825                1830                1835                1840

Ala Gly Gly Ser Leu Thr Arg His Val Thr Gln Glu Phe Val Ser Arg
                1845                1850                1855

Thr Leu Thr Thr Ser Gly Thr Leu Ser Thr His Met Asp Gln Gln Phe
        1860                1865                1870

Phe Gln Thr
    1875

<210> SEQ ID NO 5
<211> LENGTH: 8
<212> TYPE: PRT
<213> ORGANISM: Human
<220> FEATURE:
<223> OTHER INFORMATION: Amino acids 61-68 of SEQ ID NO: 3

<400> SEQUENCE: 5

Leu Leu Leu Val Gly Ala Pro Arg
 1               5

<210> SEQ ID NO 6
<211> LENGTH: 20
<212> TYPE: PRT
<213> ORGANISM: Human
<220> FEATURE:
<223> OTHER INFORMATION: Amino acids 77-96 of SEQ ID NO: 3

<400> SEQUENCE: 6

Ala Asn Arg Thr Gly Gly Leu Tyr Ser Cys Asp Ile Thr Ala Arg Gly
 1               5                  10                  15

Pro Cys Thr Arg
            20

<210> SEQ ID NO 7
<211> LENGTH: 10
<212> TYPE: PRT
<213> ORGANISM: Human
<220> FEATURE:
<223> OTHER INFORMATION: Amino acids 127-137 of SEQ ID NO: 3

<400> SEQUENCE: 7

Val Val Thr Cys Ala His Arg Tyr Glu Lys
 1               5                  10
```

```
<210> SEQ ID NO 8
<211> LENGTH: 7
<212> TYPE: PRT
<213> ORGANISM: Human
<220> FEATURE:
<223> OTHER INFORMATION: Amino acids 138-144 of SEQ ID NO: 3

<400> SEQUENCE: 8

Arg Gln His Val Asn Thr Lys
 1               5

<210> SEQ ID NO 9
<211> LENGTH: 9
<212> TYPE: PRT
<213> ORGANISM: Human
<220> FEATURE:
<223> OTHER INFORMATION: Amino acids 154-162 of SEQ ID NO: 3

<400> SEQUENCE: 9

Cys Tyr Val Leu Ser Gln Asn Leu Arg
 1               5

<210> SEQ ID NO 10
<211> LENGTH: 14
<212> TYPE: PRT
<213> ORGANISM: Human
<220> FEATURE:
<223> OTHER INFORMATION: Amino acids 185-198 of SEQ ID NO: 3

<400> SEQUENCE: 10

Phe Gly Ser Cys Gln Gln Gly Val Ala Ala Thr Phe Thr Lys
 1               5                  10

<210> SEQ ID NO 11
<211> LENGTH: 16
<212> TYPE: PRT
<213> ORGANISM: Human
<220> FEATURE:
<223> OTHER INFORMATION: Amino acids 198-214 of SEQ ID NO: 3

<400> SEQUENCE: 11

Asp Phe His Tyr Ile Val Phe Gly Ala Pro Gly Thr Tyr Asn Trp Lys
 1               5                  10                  15

<210> SEQ ID NO 12
<211> LENGTH: 11
<212> TYPE: PRT
<213> ORGANISM: Human
<220> FEATURE:
<223> OTHER INFORMATION: Amino acids 272-282 of SEQ ID NO: 3

<400> SEQUENCE: 12

Asp Glu Ile Thr Phe Val Ser Gly Ala Pro Arg
 1               5                  10

<210> SEQ ID NO 13
<211> LENGTH: 11
<212> TYPE: PRT
<213> ORGANISM: Human
<220> FEATURE:
<223> OTHER INFORMATION: Amino acids 283-293 of SEQ ID NO: 3

<400> SEQUENCE: 13

Ala Asn His Ser Gly Ala Val Val Leu Leu Lys
 1               5                  10

<210> SEQ ID NO 14
```

```
<211> LENGTH: 16
<212> TYPE: PRT
<213> ORGANISM: Human
<220> FEATURE:
<223> OTHER INFORMATION: Amino acids 328-343 of SEQ ID NO: 3

<400> SEQUENCE: 14

Asp Gly Trp Gln Asp Ile Val Ile Gly Ala Pro Gln Tyr Phe Asp Arg
 1               5                  10                  15

<210> SEQ ID NO 15
<211> LENGTH: 17
<212> TYPE: PRT
<213> ORGANISM: Human
<220> FEATURE:
<223> OTHER INFORMATION: Amino acids 344-360 of SEQ ID NO: 3

<400> SEQUENCE: 15

Asp Gly Glu Val Gly Gly Ala Val Tyr Val Tyr Met Asn Gln Gln Gly
 1               5                  10                  15

Arg

<210> SEQ ID NO 16
<211> LENGTH: 8
<212> TYPE: PRT
<213> ORGANISM: Human
<220> FEATURE:
<223> OTHER INFORMATION: Amino acids 361-368 of SEQ ID NO: 3

<400> SEQUENCE: 16

Trp Asn Asn Val Lys Pro Ile Arg
 1               5

<210> SEQ ID NO 17
<211> LENGTH: 24
<212> TYPE: PRT
<213> ORGANISM: Human
<220> FEATURE:
<223> OTHER INFORMATION: Amino acids 383-406 of SEQ ID NO: 3

<400> SEQUENCE: 17

Asn Ile Gly Asp Ile Asn Gln Asp Gly Tyr Pro Asp Ile Ala Val Gly
 1               5                  10                  15

Ala Pro Tyr Asp Asp Leu Gly Lys
             20

<210> SEQ ID NO 18
<211> LENGTH: 18
<212> TYPE: PRT
<213> ORGANISM: Human
<220> FEATURE:
<223> OTHER INFORMATION: Amino acids 427-444 of SEQ ID NO: 3

<400> SEQUENCE: 18

Gly Ile Ser Pro Tyr Phe Gly Tyr Ser Ile Ala Gly Asn Met Asp Leu
 1               5                  10                  15

Asp Arg

<210> SEQ ID NO 19
<211> LENGTH: 19
<212> TYPE: PRT
<213> ORGANISM: Human
<220> FEATURE:
<223> OTHER INFORMATION: Amino acids 445-463 of SEQ ID NO: 3

<400> SEQUENCE: 19
```

-continued

Asn Ser Tyr Pro Asp Val Ala Val Gly Ser Leu Ser Asp Ser Val Thr
 1               5                  10                  15

Ile Phe Arg

<210> SEQ ID NO 20
<211> LENGTH: 9
<212> TYPE: PRT
<213> ORGANISM: Human
<220> FEATURE:
<223> OTHER INFORMATION: Amino acids 464-472 of SEQ ID NO: 3

<400> SEQUENCE: 20

Ser Arg Pro Val Ile Asn Ile Gln Lys
 1               5

<210> SEQ ID NO 21
<211> LENGTH: 18
<212> TYPE: PRT
<213> ORGANISM: Human
<220> FEATURE:
<223> OTHER INFORMATION: Amino acids 577-594 of SEQ ID NO: 3

<400> SEQUENCE: 21

Leu Arg Pro Ile Pro Ile Thr Ala Ser Val Glu Ile Gln Glu Pro Ser
 1               5                  10                  15

Ser Arg

<210> SEQ ID NO 22
<211> LENGTH: 17
<212> TYPE: PRT
<213> ORGANISM: Human
<220> FEATURE:
<223> OTHER INFORMATION: Amino acids 597-613 of SEQ ID NO: 3

<400> SEQUENCE: 22

Val Asn Ser Leu Pro Glu Val Leu Pro Ile Leu Asn Ser Asp Glu Pro
 1               5                  10                  15

Lys

<210> SEQ ID NO 23
<211> LENGTH: 10
<212> TYPE: PRT
<213> ORGANISM: Human
<220> FEATURE:
<223> OTHER INFORMATION: Amino acids 614-623 of SEQ ID NO: 3

<400> SEQUENCE: 23

Thr Ala His Ile Asp Val His Phe Leu Lys
 1               5                  10

<210> SEQ ID NO 24
<211> LENGTH: 8
<212> TYPE: PRT
<213> ORGANISM: Human
<220> FEATURE:
<223> OTHER INFORMATION: Amino acids 652-659 of SEQ ID NO: 3

<400> SEQUENCE: 24

Phe Ser Tyr Leu Pro Ile Gln Lys
 1               5

<210> SEQ ID NO 25
<211> LENGTH: 16
<212> TYPE: PRT

```
<213> ORGANISM: Human
<220> FEATURE:
<223> OTHER INFORMATION: Amino acids 671-686 of SEQ ID NO: 3

<400> SEQUENCE: 25

Asp Ile Ala Leu Glu Ile Thr Val Thr Asn Ser Pro Ser Asn Pro Arg
 1               5                  10                  15

<210> SEQ ID NO 26
<211> LENGTH: 14
<212> TYPE: PRT
<213> ORGANISM: Human
<220> FEATURE:
<223> OTHER INFORMATION: Amino acids 822-835 of SEQ ID NO: 3

<400> SEQUENCE: 26

Ser Glu Asp Glu Val Gly Ser Leu Ile Glu Tyr Glu Phe Arg
 1               5                  10

<210> SEQ ID NO 27
<211> LENGTH: 15
<212> TYPE: PRT
<213> ORGANISM: Human
<220> FEATURE:
<223> OTHER INFORMATION: Amino acids 871-885 of SEQ ID NO: 3

<400> SEQUENCE: 27

Val Glu Ser Lys Gly Leu Glu Lys Val Thr Cys Glu Pro Gln Lys
 1               5                  10                  15

<210> SEQ ID NO 28
<211> LENGTH: 13
<212> TYPE: PRT
<213> ORGANISM: Human
<220> FEATURE:
<223> OTHER INFORMATION: Amino acids 902-914 of SEQ ID NO: 3

<400> SEQUENCE: 28

Arg Glu Ile Thr Glu Lys Gln Ile Asp Asp Asn Arg Lys
 1               5                  10

<210> SEQ ID NO 29
<211> LENGTH: 7
<212> TYPE: PRT
<213> ORGANISM: Human
<220> FEATURE:
<223> OTHER INFORMATION: Amino acids 915-921 of SEQ ID NO: 3

<400> SEQUENCE: 29

Phe Ser Leu Phe Ala Glu Arg
 1               5

<210> SEQ ID NO 30
<211> LENGTH: 16
<212> TYPE: PRT
<213> ORGANISM: Human
<220> FEATURE:
<223> OTHER INFORMATION: Amino acids 923-938 of SEQ ID NO: 3

<400> SEQUENCE: 30

Tyr Gln Thr Leu Asn Cys Ser Val Asn Val Asn Cys Val Asn Ile Arg
 1               5                  10                  15

<210> SEQ ID NO 31
<211> LENGTH: 9
<212> TYPE: PRT
<213> ORGANISM: Human
```

```
<220> FEATURE:
<223> OTHER INFORMATION: Amino acids 968-976 of SEQ ID NO: 3

<400> SEQUENCE: 31

Leu Asn Tyr Leu Asp Ile Leu Met Arg
 1               5

<210> SEQ ID NO 32
<211> LENGTH: 13
<212> TYPE: PRT
<213> ORGANISM: Human
<220> FEATURE:
<223> OTHER INFORMATION: Amino acids 977-989 of SEQ ID NO: 3

<400> SEQUENCE: 32

Ala Phe Ile Asp Val Thr Ala Ala Ala Glu Asn Ile Arg
 1               5                  10

<210> SEQ ID NO 33
<211> LENGTH: 9
<212> TYPE: PRT
<213> ORGANISM: Human
<220> FEATURE:
<223> OTHER INFORMATION: Amino acids 990-998 of SEQ ID NO: 3

<400> SEQUENCE: 33

Leu Pro Asn Ala Gly Thr Gln Val Arg
 1               5

<210> SEQ ID NO 34
<211> LENGTH: 12
<212> TYPE: PRT
<213> ORGANISM: Human
<220> FEATURE:
<223> OTHER INFORMATION: Amino acids 178-189 of SEQ ID NO: 4

<400> SEQUENCE: 34

Val Ser Val Pro Gln Thr Asp Met Arg Pro Glu Lys
 1               5                  10

<210> SEQ ID NO 35
<211> LENGTH: 13
<212> TYPE: PRT
<213> ORGANISM: Human
<220> FEATURE:
<223> OTHER INFORMATION: Amino acids 192-204 of SEQ ID NO: 4

<400> SEQUENCE: 35

Glu Pro Trp Pro Asn Ser Asp Pro Pro Phe Ser Phe Lys
 1               5                  10

<210> SEQ ID NO 36
<211> LENGTH: 13
<212> TYPE: PRT
<213> ORGANISM: Human
<220> FEATURE:
<223> OTHER INFORMATION: Amino acids 205-217 of SEQ ID NO: 4

<400> SEQUENCE: 36

Asn Val Ile Ser Leu Thr Glu Asp Val Asp Glu Phe Arg
 1               5                  10

<210> SEQ ID NO 37
<211> LENGTH: 12
<212> TYPE: PRT
<213> ORGANISM: Human
<220> FEATURE:
```

```
<223> OTHER INFORMATION: Amino acids 301-312 of SEQ ID NO: 4

<400> SEQUENCE: 37

Thr Gln Asp Tyr Pro Ser Val Pro Thr Leu Val Arg
 1               5                  10

<210> SEQ ID NO 38
<211> LENGTH: 12
<212> TYPE: PRT
<213> ORGANISM: Human
<220> FEATURE:
<223> OTHER INFORMATION: Amino acids 402-413 of SEQ ID NO: 4

<400> SEQUENCE: 38

Arg Gly Glu Val Gly Ile Tyr Gln Val Gln Leu Arg
 1               5                  10

<210> SEQ ID NO 39
<211> LENGTH: 18
<212> TYPE: PRT
<213> ORGANISM: Human
<220> FEATURE:
<223> OTHER INFORMATION: Amino acids 414-431 of SEQ ID NO: 4

<400> SEQUENCE: 39

Ala Leu Glu His Val Asp Gly Thr His Val Cys Gln Leu Pro Glu
 1               5                  10                  15

Asp Gln Lys

<210> SEQ ID NO 40
<211> LENGTH: 14
<212> TYPE: PRT
<213> ORGANISM: Human
<220> FEATURE:
<223> OTHER INFORMATION: Amino acids 432-445 of SEQ ID NO: 4

<400> SEQUENCE: 40

Gly Asn Ile His Leu Lys Pro Ser Phe Ser Asp Gly Leu Lys
 1               5                  10

<210> SEQ ID NO 41
<211> LENGTH: 16
<212> TYPE: PRT
<213> ORGANISM: Human
<220> FEATURE:
<223> OTHER INFORMATION: Amino acids 446-461 of SEQ ID NO: 4

<400> SEQUENCE: 41

Met Asp Ala Gly Ile Ile Cys Asp Val Cys Thr Cys Glu Leu Gln Lys
 1               5                  10                  15

<210> SEQ ID NO 42
<211> LENGTH: 15
<212> TYPE: PRT
<213> ORGANISM: Human
<220> FEATURE:
<223> OTHER INFORMATION: Amino acids 531-545 of SEQ ID NO: 4

<400> SEQUENCE: 42

Tyr Glu Gly Gln Phe Cys Glu Tyr Asp Asn Phe Gln Cys Pro Arg
 1               5                  10                  15

<210> SEQ ID NO 43
<211> LENGTH: 16
<212> TYPE: PRT
<213> ORGANISM: Human
```

-continued

<220> FEATURE:
<223> OTHER INFORMATION: Amino acids 631-646 of SEQ ID NO: 4

<400> SEQUENCE: 43

Ser Cys Val Gln Cys Gln Ala Trp Gly Thr Gly Glu Lys Lys Gly Arg
1               5                   10                  15

<210> SEQ ID NO 44
<211> LENGTH: 28
<212> TYPE: PRT
<213> ORGANISM: Human
<220> FEATURE:
<223> OTHER INFORMATION: Amino acids 675-702 of SEQ ID NO: 4

<400> SEQUENCE: 44

Asp Glu Asp Asp Asp Cys Thr Tyr Ser Tyr Thr Met Glu Gly Asp Gly
1               5                   10                  15

Ala Pro Gly Pro Asn Ser Thr Val Leu Val His Lys
            20                  25

<210> SEQ ID NO 45
<211> LENGTH: 12
<212> TYPE: PRT
<213> ORGANISM: Human
<220> FEATURE:
<223> OTHER INFORMATION: Amino acids 845-856 of SEQ ID NO: 4

<400> SEQUENCE: 45

Gln Glu Val Glu Glu Asn Leu Asn Glu Val Tyr Arg
1               5                   10

<210> SEQ ID NO 46
<211> LENGTH: 16
<212> TYPE: PRT
<213> ORGANISM: Human
<220> FEATURE:
<223> OTHER INFORMATION: Amino acids 916-930 of SEQ ID NO: 4

<400> SEQUENCE: 46

Val Ala Pro Gly Tyr Tyr Thr Leu Thr Ala Asp Gln Asp Asp Ala Arg
1               5                   10                  15

<210> SEQ ID NO 47
<211> LENGTH: 13
<212> TYPE: PRT
<213> ORGANISM: Human
<220> FEATURE:
<223> OTHER INFORMATION: Amino acids 946-958 of SEQ ID NO: 4

<400> SEQUENCE: 47

Val Pro Leu Phe Ile Arg Pro Glu Asp Asp Asp Glu Lys
1               5                   10

<210> SEQ ID NO 48
<211> LENGTH: 14
<212> TYPE: PRT
<213> ORGANISM: Human
<220> FEATURE:
<223> OTHER INFORMATION: Amino acids 990-1003 of SEQ ID NO: 4

<400> SEQUENCE: 48

Asp Val Val Ser Phe Glu Gln Pro Glu Phe Ser Val Ser Arg
1               5                   10

<210> SEQ ID NO 49
<211> LENGTH: 12

```
-continued

<212> TYPE: PRT
<213> ORGANISM: Human
<220> FEATURE:
<223> OTHER INFORMATION: Amino acids 1061-1072 of SEQ ID NO: 4

<400> SEQUENCE: 49

Leu Leu Glu Leu Gln Glu Val Asp Ser Leu Leu Arg
 1               5                  10

<210> SEQ ID NO 50
<211> LENGTH: 18
<212> TYPE: PRT
<213> ORGANISM: Human
<220> FEATURE:
<223> OTHER INFORMATION: Amino acids 1196-1214 of SEQ ID NO: 4

<400> SEQUENCE: 50

Val Cys Ala Tyr Ala Gln Gly Glu Gly Pro Tyr Ser Ser Leu Val Ser
 1               5                  10                  15

Cys Arg

<210> SEQ ID NO 51
<211> LENGTH: 9
<212> TYPE: PRT
<213> ORGANISM: Human
<220> FEATURE:
<223> OTHER INFORMATION: Amino acids 1273-1281 of SEQ ID NO: 4

<400> SEQUENCE: 51

Val Leu Val Asp Asn Pro Lys Asn Arg
 1               5
```

COMPOUNDS

The present invention is related to an antibody, or a derivate, or a fragment thereof, having a binding structure for a target structure displayed in, and on the cell surface of, human gastrointestinal epithelial tumour cells and in a subpopulation of normal human gastrointestinal epithelial cells; and to a target structure displayed in, or on the surface of tumour cells; vaccine compositions; pharmaceutical compositions; as well as methods related to human malignant diseases.

BACKGROUND OF THE INVENTION

Surgery is the primary treatment of colorectal cancer leading to five-year survival rates of 90 to 40 percent depending on the state of tumour progression from Dukes Stage A to C. Conventional adjuvant therapy that includes radiation therapy and chemotherapy has been able to reduce the death rates further by approximately 30 percent (1). Despite these achievements cancer of the colon and rectum is one of the major causes of death in human cancer. Immunological therapy has been extensively attempted. However, colon cancer has generally been resistant to immunotherapy and is considered to be of low immunogenicity. Patients with colon cancer neither respond to IL-2 treatment or adoptive transfer of in vitro cultured tumour infiltrating lymphocytes otherwise active in patients with immunogenic malignancies such as melanoma. Most encouraging however, Riethmüller et al. reported a 32 percent decreased seven-year death rate for Dukes Stage C colorectal cancer treated after primary tumour resection with a naked murine mAb directed to a tumour and normal epithelial associated antigen (Ep-CAM) (2), indicating that other immunotherapeutic modalities could be effective.

A significant improvement of adjuvant immunotherapy and of the treatment of more advanced stages of cancer should require a more potent effector mechanism than provided by a naked mAb. In principle, an increased potency should require an increased tumour selectivity of the targeting antibody.

The limited number of colon cancer associated antigens defined today have been discovered using hybridoma produced murine mAbs resulting from xenogenic immunisations with human tumours (3).

The use of large phage display libraries for the identification of novel tumour-associated antigens can be expected to significantly speed up the process of finding target molecules useful for tumour immunotherapy and diagnosis. Such identification of target molecules could be accomplished by the selection and screening of antibody phage libraries on cultured tumour cells and tissue sections to generate specific reagents defining in vitro and in vivo expressed antigens (4). The phage display technology has been established as an efficient tool to generate monoclonal antibody reagents to various purified antigens, and the construction and successful selection outcome from immune, naive and synthetic antibody phage libraries have been described in several studies (5).

Non-immune libraries are favourable with respect to their general applicability, making unique libraries for every single target unnecessary. On the other hand, sufficiently large and high quality non-immune libraries are difficult to construct and a target discovery process using these libraries should require efficient subtractive selection methods when based on complex antigens.

A phage library of a more moderate size has now been constructed from a near human primate immunised with complex human antigens. This represents an approach that takes advantage of an in vivo pre-selected repertoire. Such libraries should be enriched for specificities to tumour specific epitopes in a reduced background reactivity to xenogeneic antigens (6). Furthermore, as compared to the mouse, primate antibodies demonstrating close sequence homology with human antibodies should not be immunogenic in man (7).

Novel primate antibodies from a phage library that define selectively expressed colon cancer associated antigens have now been identified. The therapeutic potential, demonstrated by T cell mediated killing of cultured colon cancer cells coated with two of these antibodies fused to engineered superantigens, is comparable with superantigens fused to murine Fab fragment specific for colon cancer associated antigens such as EP-CAM, for which there has previously been established the therapeutic capacity in experimental systems (8).

There is also provided a method for efficient positive and subtractive cell selection of phage antibodies that should facilitate future identification of novel phenotype specific antigens including tumour associated antigens using antibodies from large phage libraries.

BRIEF SUMMARY OF THE INVENTION

The present invention is related in a first aspect to an antibody, or a derivative or a fragment thereof, having a binding structure for a target structure displayed in, and on the cell surface of, human gastrointestinal epithelial tumour cells and in a subpopulation of normal human gastrointestinal epithelial cells, said binding structure comprising the complementarity determining region (CDR) sequences in the light chain comprising essentially the amino acids number 23–33 (CDR1), 49–55 (CDR2), 88–98 (CDR3) of the amino acid sequence shown in SEQ ID NO:2, and the CDR sequences in the heavy chain comprising essentially the amino acids number 158–162 (CDR1), 177–193 (CDR2), 226–238 (CDR3) of the amino acid sequence shown in NO: 2, or other binding structures with similar unique binding properties.

In one embodiment the antibody is phage selected. In another embodiment the sequences are of *Macaca fascicularis* origin. A further embodiment of the invention is a derivative of said antibody, which derivative is of human origin. The sequences preferably have an identity of at least 84% to corresponding sequences of human origin. Preferably, the antibody has low immunogenicity or non-immunogenicity in humans.

In a further embodiment, the antibody has been derivatised by genetically linking to other polypeptides, and/or by chemical conjugation to organic or non-organic chemical molecules, and/or by di-, oligo- or multimerisation.

In still a further embodiment, said antibody is genetically linked or chemically conjugated to cytotoxic polypeptides or to cytotoxic organic or non-organic chemical molecules.

In a further embodiment, said antibody is genetically linked or chemically conjugated to biologically active molecules.

In still a further embodiment, said antibody is genetically linked or chemically conjugated to immune activating molecules.

In another embodiment, said antibody has been changed to increase or decrease the avidity and/or affinity thereof.

In still another embodiment, said antibody has been changed to increase the production yield thereof.

In a further embodiment, said antibody has been changed to influence the pharmacokinetic properties thereof.

In still a further embodiment, said antibody has been changed to give new pharmacokinetic properties thereto.

In a further embodiment, said antibody is labeled and the binding thereof is inhibited by an unlabeled form of said antibody and not by other binding structures, and not inhibiting the binding of other binding structures having other specificities.

A further embodiment is an antibody, the binding structure of which recognizes a non-reduced form of α6β4 integrin.

In another aspect the invention relates to a target structure displayed in, or on the surface of, tumour cells, said target structure a) having the ability of being specifically blocked by and to specifically block the binding structure of an antibody as defined in any one of claims 1–14, and other binding structures with similar binding specificities, b) being displayed in, and on the surface of, human gastrointestinal epithelial cells, c) having substantial homology with α6 and/or β4 integrin chains or variants thereof, representing a shared or unique epitope, d) being highly expressed on the surface of tumour cells, and e) being a target for cytotoxic effector mechanisms.

By substantial homology in this context is meant homology in those parts of the target structure which are relevant for the binding of the antibody.

In one embodiment of said target structure, the binding structure is labeled and the binding thereof is inhibited by an unlabeled form of said binding structure and not by other binding structures, and not inhibiting the binding of other binding structures having other binding specificities.

In a further embodiment of said target structure said binding structure comprises one or more of the complementarity determining region (CDR) sequences comprising essentially the amino acids number 23–33, 49–55, 88–98, 158–162, 177–193, 226–238 of the amino acid sequence shown in SEQ ID NO:2, or other binding structures with similar unique binding properties.

In still a further embodiment of said target structure said binding structure is an antibody, which antibody in a further embodiment comprises the variable region of a light chain comprising essentially the amino acids number 1–109 of the amino acid sequence shown in SEQ ID NO:2, and the variable region of a heavy chain comprising essentially the amino acids number 128–249 of the amino acid sequence shown in SEQ ID NO: 2.

Said target structure is in a further embodiment expressed homogenously in human colonic epithelial cells and less in pancreatic duct and bile duct cells.

In still a further embodiment, the expression of said target structure is correlated to gastrointestinal epithelial differentiation.

In another embodiment, said target structure comprises the amino acid sequence of α6β4 integrin, of which the α6 part is shown in SEQ ID NO: 3 and the β4 part is shown in SEQ ID NO: 4. Another embodiment of the target structure comprises homo- or heteromonomers or homo- or heteromultimers of said α6β4 integrin and/or of said one or more fragments and/or variants and/or subunits thereof. Preferably, said target structure has an apparent molecular weight in its non-reduced form of from 90 to 140 kDa, most preferred fro 80 to 160 kDa.

In still further embodiments the target structure comprises a peptide or polypeptide(s) comprising essentially any one of the amino acid sequences shown in SEQ ID NOs: 5–51, or comprises a molecule complexed to said polypeptide(s).

In the case of a target structure comprising amino acid sequences from the α6β4 integrin, said target structure may in a further embodiment be recognised, exclusively or not, in its non-reduced form by the binding structure comprised by the antibody as defined above.

The invention relates in a further aspect to a substance which binds to the target structure as defined above, which substance is an organic chemical molecule or a peptide. In one embodiment, said substance is an anti-idiotype of said target structure. Said anti-idiotype may be specifically blocked by and specifically block a binding structure having similar binding specificity for said target structure.

In a still further aspect, the invention relates to a substance that blocks the function of the target structure as defined above, which substance is an organic molecule or a peptide.

In another aspect, the invention relates to a binding structure which recognises a target structure as defined above and which is of an organic chemical nature.

In a further aspect, the invention relates to a pharmaceutical composition comprising as an active principle an antibody as defined above, or a target structure as defined above, or a substance as defined above.

In still a further aspect, the invention is related to a vaccine composition comprising as an active principle abn antibody as defined above, or a target structure as defined above, or a substance as defined above.

In a further aspect, the invention is related to a method of therapy for treating conditions based on an anti-angiotenic mechanism, whereby an antibody as defined above, or a target structure as defined above, or a substance as defined above, is administered to a human subject.

In another aspect, the invention is related to a method of treating human metastatic diseases, wherein an antibody as defined above is administered to a human subject.

In a further aspect the invention is related to a method of in vitro histopathological diagnosis and prognosis of human malignant disease, whereby a sample is contacted with an antibody as defined above and an indicator.

Embodiments of said method comprise tumour typing, tumour screening, tumour diagnosis and prognosis, and monitoring premalignant conditions.

In still a further aspect, the invention is related to a method for in vitro diagnosis and prognosis of human malignant disease, whereby concentrations in bodily fluids of an antigen comprising a target structure, as defined above, or an anti-idiotype of said target structure, as defined above, is assayed.

A further aspect of the invention is related to a method for in vitro diagnosis and prognosis of human malignant disease, whereby concentrations in bodily fluids of an antibody as defined above is assayed.

A still further aspect of the invention is related to a method for in vitro diagnosis and prognosis of human malignant disease, whereby concentrations in bodily fluids of a complex of a) an antigen comprising a target structure, as defined above, or an anti-idiotype of said target structure, as defined above, and b) an antibody, as defined above, is assayed.

In a still further aspect, the invention is related to a method for in vivo diagnosis and prognosis of human malignant disease, whereby the localisation of an antibody, as defined above, to tumour deposits in a human subject is determined. Said antibody is preferably administered to the subject before the determination. In one embodiment said antibody is accumulated in tumour deposits. In a further embodiment, said method is quantitative.

Another aspect of the invention is related to a method for therapy of human malignant disease, whereby an antibody, as defined above, is administered to a human subject. In one embodiment of this method said antibody has been changed by being genetically linked to molecules giving the combined molecule changed pharmacokinetic properties. In another embodiment said antibody has been changed by being derivatised.

DETAILED DESCRIPTION OF THE INVENTION

The identification of novel tumour associated antigens (TAAs) is pivotal for the progression in the fields of tumour immunotherapy and diagnosis. In relation to the present invention, there was first developed, based on flow cytometric evaluation and use of a mini-library composed of specific antibody clones linked to different antibiotic resistance markers, methods for positive and subtractive selection of phage antibodies employing intact cells as the antigen source. An scFv phage library ($2.7 \times 10^7$) was constructed from a primate (*Macaca fascicularis*) immunised with pooled human colon carcinomas. This library was selected for three rounds by binding to Colo205 colon adenocarcinoma cells, and proteolytic elution followed by phage amplification.

Several antibodies reactive with colon carcinomas and with restricted reactivity with a few epithelial normal tissues were identified by immunohistochemistry. One clone, A3 scFv, recognised an epitope that was homogeneously expressed in 11/11 of colon and 4/4 pancreatic carcinomas studied and normal tissue expression restricted to subtypes of epithelia in the gastrointestinal tract. The A3 scfv had an apparent overall affinity about 100-fold higher than an A3 Fab, indicating binding of scFv homodimers. The cell surface density of the A3 epitope, calculated on the basis of Fab binding, was exceptionally high, approaching 3 million per cell.

Efficient T cell mediated killing of colon cancer cells coated with A3 scFv fused to the low MHC class II binding superantigen mutant SEA(D227A) is also demonstrated. The identified A3 molecule thus represents a TAA with properties that suggests its use for immuno-therapy of colon and pancreatic cancer.

DISCUSSION

In relation to the present invention, efficient protocols for phage selection to be used for the identification of cell phenotype specific antibody fragments from large phage libraries was developed. The target specificities for the applications as exemplified were for colon tumour associated antigens.

First the frequency of pIII-scFv fusion protein surface display in the phage population using the herein presented phagemid construct for phage propagation was analysed. A higher level of C215 scFv display was achieved as compared to previous reports. This should favour subtractive selection efficiency, but also increases the probability of avidity selection of low affinity antibodies from libraries.

Specificity of C215 scFv phage binding to colon adenocarcinoma Colo205 cells was clearly demonstrated. Bound phage could be efficiently eluted by use of the protease Genenase that specifically cleaves a target sequence between the phage protein III and the scFv antibody leaving the cells intact after elution. This non-chemical elution method should equally efficiently elute phage antibodies irrespectively of their binding affinity and only phage bound by scFv interactions, adding to the specificity of the process.

The enrichment achieved after three selection rounds on Colo205 cells (500 000×) using this selection protocol was similar to that reported by other investigators for selections on complex antigens.

After verifying the performance of the various methodological steps the combined technology was applied to library selections using Colo205 cells.

The library was constructed from a near human species immunised with human tumours. The antibody pool generated this way would potentially include affinity matured antibodies to tumour specific antigens in a limited background of xeno reactivities to widespread normal human tissue antigens (6). The antibodies identified recognised tumour and tissue differentiation antigens with restricted normal tissue distribution. All of the selected antibodies identified as colon cancer tissue reactive in the primary screening also reacted with viable Colo205 cells in flow cytometry. This restriction to cell surface specificities should reflect the selection process and not the composition of the library, since a suspension of a mixture of tumour tissue components was used for the immunisation.

In a similar previous study extra- and intracellular specificities were identified in an anti-melanoma library produced the same way and selected using tissue sections as the antigen source (4). Tissue sections of resected human colorectal tumours and normal colon (mounted in the same well) were used for the primary screening using immunohistochemistry to assure the clinical relevance of the selected specificities, to increase the efficiency and to obtain more qualitative information as compared to flow cytometric screening.

The selected antibodies could be classified into four antibody specificity groups, distinguished by their reactivity patterns to epithelia in different organs (see Example 1, Table 1). Among these specificity groups, A3 scFv identified the most tumour selective antigen. This A3 TAA was highly, homogeneously and frequently expressed in samples of primary and metastatic colon cancer and of pancreatic cancer. Furthermore, its cell surface expression level as determined with the A3 Fab fusion protein (3 millions epitopes/cell) was exceptionally high and permissive for cell surface mediated cytotoxic effects.

Few, if any, of the frequently expressed human tumour antigens defined are tumour specific, but are commonly related to tissue differentiation such as A3 and the Ep-CAM. However, upregulated expression of these antigens in tumours should provide a basis for a therapeutically active dose window. The availability from the circulation of normal tissue compartments expressing the antigen may also be more restricted due to limited capillary permeability and their site of expression in the body (e.g. the exposure of the apical side of gut epithelial cells to circulating antibodies should be very limited).

The clinical experience with the pan-epithelial Ep-CAM reactive 17-1A mAb supports the feasibility to identify an effective non-toxic antibody dose. The restricted expression in epithelia of all of the selected scFv clones in this work, indicate that these clones in principal could be evaluated as candidates for immuno-therapeutic applications analogously to the 17-1A, e.g. as full-length mAbs. However, a particular advantage for the A3 TAA as compared to the Ep-CAM is the lack of expression in most normal epithelia such as of the lung and kidney, although the expression in the colon is similar.

The tissue distribution to subtypes of normal epithelia is supported by the selective expression in subtypes of carcinomas originating from the gastro-intestinal tract (see Example 2, Table 2).

Several of the previously well-known colon cancer associated antigens (CEA, CA50, CA19-9, CA242, Tag-72) (3) are expressed equally or more restrictedly in normal tissues as compared to the A3 epitope. However, in contrast to the A3 and the C215 Ep-CAM they are more heterogeneously expressed in tumours.

Use of antibodies to the Ep-CAM has demonstrated good clinical results including a survival advantage for colorectal cancer patients in an adjuvant setting (2). With the objective to induce tumour responses even in more advanced stage patients, the introduction of potent effector molecules in conjunction with this antibody will challenge the "normal tissue resistance" seen in the treatment with the naked 17-1A mAb. Preclinically, this could be studied in model systems using toxin-conjugated antibodies specific to the murine version of this antigen or animals transgenic for human colon cancer associated antigens.

Previously, antibody immunotoxins have been successfully used to cure mice in models with metastatically growing tumours expressing xeno (human) tumour antigens not expressed in mouse tissues (10). However, the TAAs used are truly tumour specific and the models do not reflect the potential for normal tissue targeted toxicity.

In previous studies we have reported the potential of superantigens as immunostimulatory toxins for tumour immunotherapy (8). Antibody mediated targeting of superantigens attracted large numbers of cytotoxic and cytokine-producing T cells to the tumour site. The superantigen SEA(D227A), mutated for low MHC class II binding affinity, was genetically linked to tumour targeting antibodies. This "tumour-selective" agent was applied to recruit T cells independent of MHC expression in the tumour, thus short-cutting the problems of MHC down regulation and polymorphism that represent significant obstacles for other active immunotherapeutic approaches.

The mini-library of the established "tumour-selective", 1F scFv phage, the "broadly-reactive" C215 phage and the non-specific D1.3 phage antibody clones was an essential tool for the development of protocols for efficient subtractive cell selection. A requirement for this selection principle is that the negative selection is followed by positive selection before phage rescue and amplification, due to the high frequency of non-displaying phage particles. Alternatively, non-displaying phage can be made non-infective by selective proteolysis (G. Winter, pers. comm.) Such a technique may allow the generation of "inert libraries", i.e. libraries that have been extensively negatively preselected (e.g. towards a cell in a resting state or a transfectable parental cell).

In conclusion, the "non-wanted" model phage specificity could selectively be subtracted from the phage population by a factor of approx. 100 for each selection round. Future subtractive selections using the developed protocol in combination with the use of large non-immune phage libraries for identification of differentially expressed cell surface antigens will demonstrate whether such an approach prove to be superior to the strategy we used in this study, i.e. positive selection using an in vivo pre-selected immune repertoire, including restrictions and biases such as immunodominance (4). The low affinity and high epitope density demonstrated for the A3 Fab binding to tumour cells as compared to the A3 scFv fusion protein suggests formation of scFv multimers that interact with epitopes that cluster on cell surfaces. Higher affinity monovalent variants of A3 Fab or alternatively, stable divalent constructs such as full-length A3 Fv grafted mAbs compatible with the putative low immunogenicity of A3 should be developed. Such constructs would be suitable for targeting of appropriate effector molecules to this highly expressed gastro-intestinal tumour associated antigen.

The invention is further illustrated in the following non-limiting experimental part of the description.

EXMPERIMENTAL PART

Materials and Methods

Animals

Cynomolgus Macaque (*Macaca fascicularis*) monkeys were kept and immunised at the Swedish Institute for Infectious Decease Control (SIIDC), Stockholm. Water and food were always available ad libitum. Four monkeys were immunised subcutaneously with 2 ml of a crude suspension of colon cancer tissues in 10% normal cynomolgus serum in PBS. Booster doses were given day 21, 35, and 49. Antibody responses were demonstrated in two monkeys where the antigen had been admixed with alum adjuvant. All animals were kept according to Swedish legislation and the experiments were approved by the local ethical committees.

Tissues and Cells

Human tumours and normal tissue samples were obtained from Lund University Hospital and Malmö General Hospital, Sweden. The human colorectal cell line Colo205, the human B cell lymphoma cell line Raji and the murine B16 melanoma cell line were from the American Tissue Culture Collection (ATCC, Rockville, Md.). The mouse melanoma B16-C215$^+$ cells transfected with the expression vector pKGE839 containing the Ep-CAM-1 gene (C215) has been described previously (9).

The human cells were cultured in RPMI 1640 medium (Gibco, Middlesex, UK) supplemented with 10% heat inactivated foetal bovine serum (Gibco) and 0.1 mg/ml gentamycin sulphate (Biological Industries, Kibbutz Beit Haemek, Israel). The mouse cells were cultured in medium additionally supplemented with 1 mM glutamine (Hyclone, Cramlington, UK), $5\times10^{-5}$ M β-mercaptoethanol (ICN, Costa Mesa, Calif.), 0.2% NaHCO$_3$ (Seromed Biochrome, Berlin, Germany), $1\times10^{-2}$ M HEPES (HyClone, UT) and $1\times10^{-3}$ M sodium pyrovate (HyClone). The cells were repeatedly tested for *Mycoplasma* contamination with Gene-Probe *Mycoplasma* T. C. test (San Diego, Calif.).

Phagemid Vector and Phase Library Construction

Total spleen RNA was extracted from one of the responding monkeys using an RNA isolation kit from Promega (Mannheim, Germany) and cDNA was amplified using an RNA PCR kit from PE Biosystems (Stockholm, Sweden). The primers for cDNA synthesis of lambda light chain and heavy chain genes and for the assembly of these genes to scFv genes have been reported previously (4). The scFv cDNA was ligated into a phagemid vector (4) in fusion with the residues 249–406 of the M13 gene III. The scFv-gIII gene was expressed from a phoA promoter and the resulting protein was directed by the *E. coli* heat stable toxin II signal peptide.

Repeated electroporations of 7 µg library vector with scFv gene inserts resulted in a total of $2.7 \times 10^7$ primary transformed *E. coli* TG-1 growing as colonies on minimal agar plates. The colonies were scraped from the plates and grown in 2×YT at 150 rpm and 37° C. for 1 h. The culture was superinfected with M13K07 helper phage (Promega) in 50 times excess. Ampicillin to a concentration of 100 mg/l was added and the culture grown for a further hour. After addition of kanamycin to a concentration of 70 mg/l, the culture was grown for 15 h at 30° C. and 250 rpm. The phage particles were harvested from the culture supernatant using two repeated PEG/NaCl precipitations. The precipitated phage was resolved in PBS 1% BSA.

Western Blot Analysis

A two-fold dilution series of scFv-C215 phage particles (from an undiluted stock of PEG-precipitated/concentrated phage) was applied to separation on a reducing 12% polyacrylamide gel with 1% SDS and 2% β-mercaptoethanol. The proteins were transferred to a nitrocellulose membrane (Bio-Rad, Hercules, Calif.) by electrophoresis. The membrane was blocked with 5% low-fat milk (Semper AB, Stockholm, Sweden) and then incubated with a rabbit antiserum against a protein III derived peptide sequence, AEGDDPAKAAFNSLQASATEC, conjugated to keyhole limpet hemocyanin. Secondary horse radish peroxidase (HRP) conjugated goat-anti-rabbit antibodies (Bio-Rad) were incubated for 30 min. Between all steps the membrane was washed 3 times during 5 min in PBS/0.5% Tween 20. The membrane was incubated in substrate (Amersham Pharmacia Biotech, Little Chalfon Buckinghamshire, UK) for one min. A light sensitive film (ECL hyperfilm, Amersham) was exposed to the membrane and developed for 0.5–5 min.

Similarly, to analyse the integrity of purified Fab (A3, including cynomolgus CH1 and Clambda domains), scFv- and Fab (including murine CH1 and Ckappa)-SEA(D227A) fusion proteins (produced as described previously (9)), 12% SDS-PAGEs were performed. The membranes with transferred proteins were incubated with purified polyclonal rabbit anti-SEA antibodies followed by the reagent steps described above.

Model and Library Phase Selection on Cells

Phage suspensions of the lambda light chain library (or of model phage), $10^{12}$ in 100 µl PBS/1% BSA, were incubated with 3 million Colo205 cells for 1 h on ice. The cells were washed 3 times including a 10-min incubation using 2 ml PBS/1% BSA for each wash. The phage were eluted by adding 50 µl of 33 µg/ml Genenase to the cell pellet and incubated for 15 min. Genenase, which is a subtilisin BPN' mutant, S24C/H64A/E156S/G169A/Y217L, was kindly provided by Dr. Poul Carter (San Francisco, Calif.). After centrifugation the supernatant was transferred to a new tube and 250 µl 1% BSA in PBS was added. To rescue and amplify the selected library (and the model phage particles in the multi-pass experiment), the eluted phage particles were allowed to infect 1 ml, *E. coli* DH5αF' ($OD_{600\ nm}$=1.0). The infected bacterial culture was diluted 100 times with 2×YT supplemented with the proper antibiotic and cultured until an OD >1.0 (up to two days).

Finally, to produce soluble scFv the amber suppressor strain HB2151 of *E. coli* was infected with the selected library from the second and third round. After growth on agar plates containing ampicillin, single colonies were cultured in 96 Micro well plates in 2×YT medium supplemented with ampicillin at 30° C. for 17 h. After centrifugation, removal of the supernatant to which an equal volume of PBS/1% BSA was added, individual scFvs were analysed for immunoreactivity to sections of human tumours and normal tissues. Briefly, the C-terminal tag, ATPAKSE, was detected using a rabbit antiserum followed by biotinylated goat anti-rabbit antibodies (DAKO A/S, Copenhagen, Denmark) and StreptABComplex HRP (DAKO A/S) (see "Immunohistochemistry").

Immunohistochemistry

Frozen cryosections (8 µm) were air-dried on slides, fixed in acetone at −20° C. for 10 min and rehydrated in 20% foetal bovine serum in PBS (FBS). Endogenous biotin was blocked with avidin (diluted 1/6) for 15 min and then with biotin (diluted 1/6) for 15 min (Vector Labora-tories, Burlingame, Calif.). Affinity purified and biotinylated rabbit anti-SEA antibodies, 5 µg/ml, were incubated for 30 min followed by StreptABComplex HRP (DAKO A/S, Copenhagen, Denmark), 1/110 diluted in 50 mM Tris pH 7.6 for 30 min. Between all steps the sections were washed 3 times in TBS. The staining reaction was developed for 8 min in 0.5 mg/ml 3,3'-diaminobenzidine tetrahydrochloride (Sigma) dissolved in Tris pH 7.6 with 0.01 percent $H_2O_2$. After 10 min counterstaining in 0.5% methyl green, the slides were rinsed for 10 min in tap water and gradually dehydrated in 70–99% ethanol and xylene before mounting in DPX medium (Sigma).

Flow Cytometry

The Colo205 colon cancer cells were dissociated with 0.02% w/v EDTA and washed with PBS. To follow the development of an antibody response in the monkeys the cells were incubated consecutively with diluted serum, for 1 h at 4° C., biotinylated rabbit anti-human IgG antibodies (Southern Biotechnology Ass. Inc., Al, USA) for 30 min, and finally with avidin-PE (Becton Dickinson, Mountain View, Calif.) for 30 min.

The binding of model phage to the cells was analysed using rabbit-anti-M13 antibodies (produced by immunisation of rabbits with M13 particles) and FITC conjugated donkey anti-rabbit antibodies (Amersham Pharmacia Biotech). The binding of antibodies fused to SEA(D227A) was detected using biotinylated rabbit anti-SEA antibodies and avidin-PE. All reagents were diluted in PBS/1% BSA. The cells were washed twice with PBS/1% BSA after incubations with reagents and three times including 10 min incubations after binding of phage particles.

Flow cytometric analysis was performed using a FACSort flow cytometer (Becton Dickinson).

Affinity Determination on Cultured Cells

A3 scFv-SEA(D227A), A3 Fab-SEA(D227A) and 1F scFv SEA(D227A) fusion proteins, 80 µg of each protein, were labelled with iodine as described by Bolton and Hunter to a specific activity of 10–15 µCi/µg. Colo205 cells and Raji cells, 30 000/sample were incubated with the iodinated fusion protein at 100 µl/tube in a two-fold dilution series in 1% BSA for 1 h and then washed three times in PBS before measuring bound activity. The concentration of added and bound fusion protein was used for Scatchard analysis. The background binding to the Raji cells was subtracted to calculate the specific binding to the Colo205 cells.

Cytotoxicity Assay

The T cell dependent cytotoxicity of the super-antigen fusion protein (superantigen antibody dependent cellular cytotoxicity, SADCC) was measured in a standard 4 h chromium-release assay employing $^{51}Cr$-labelled Colo205 cells as target cells and human T cells as effector cells (9). The percent specific lysis was calculated as:

$$100 \times \frac{\text{cpm experomental release} - \text{cpm background release}}{\text{cpm total release} - \text{cpm background release}}$$

EXAMPLE 1

Generation of Tumour Binding Monoclonal Cynomolgus Antibodies

Cynomolgus monkeys, *Macaca fascicularis* (four individuals) were repeatedly immunised with a suspension of human colon carcinomas four times every other week. The gradual development of an antibody response in the monkeys was followed by flow cytometric staining of cultured colorectal cells, Colo205, using dilution series of the preimmune and immune sera. An IgG antibody response was elicited only when alum precipitated tumour tissue suspensions were used (two individuals).

The monkey with the highest binding level of immune to preimmune serum antibodies was used for the construction of a large combinatorial scFv phage library of approximately $2.7 \times 10^7$ (estimated from the number of primary transformants). The primate phage library was selected using Colo205 cells. The total phage yield (eluted/added number of phage counted as colony forming units, CFU) from three consecutive selection rounds increased gradually from $1.9 \times 10^{-7}$, $1.4 \times 10^{-5}$, to $1.2 \times 10^{-3}$. Five percent (12/246) of the monoclonal soluble scFv:s produced from the phage library after the third round of selection were demonstrated to bind to sections of a human colorectal cancer tissue and to intact Colo205 cells by flow cytometry. All of the selected antibodies demonstrated individually unique nucleic acid sequences according to Hinf I restriction patterns analysed by 1% agarose gel electrophoresis.

The antibody genes were amplified by polymerase chain reaction using 5 µl of bacterial cultures and primers complementary to regions 5' and 3' to the scFv gene in the phagemid vector (regions in the phoA promoter and in the M13 gene III).

The Selected scFv Demonstrate Individually Unique Reactivity with Epithelia in Normal Tissues The colorectal cancer reactive scFv's were classified into specificity groups based on their immunohistochemical reactivity pattern with normal tissues (Table 1). The antibodies studied in detail were A3 scFv (and A3 scFv-SEA (D227A)), A10 scFv, 3D scFv and 1D scFv. The representative antibodies could be distinguished from each other by their fine specificity to epithelia in different organs and by their binding to leukocytes. The 1D scFv strongly reacted with gut epithelia and was the only antibody that reacted with cells of polymorph nuclear granulocyte morphology. The 1D scFv also differed from the other antibodies by staining the luminal surface of kidney tubuli and collecting ducts whereas the A10 scFv reacted homogeneously (nonpolarly) with these epithelial cells and 3D scfv and A3 scFv were negative. 1D, A10 and 3D, but not A3 scFv also reacted with macrophage-like cells in the lung.

A fifth group of antibodies, not extensively evaluated and thus not included in Table 1, reacted with colon epithelia, leukocytes and Kuppfer cells in the liver. The A3 scFv stands out as demonstrating the most restricted reactivity with the panel of normal tissues used. The most prominent normal tissue reactivity of the A3 was staining of normal colon epithelium. Weak staining were also detected in small ducts of the pancreas and bile ducts of the liver and of substructures in small bowel epithelia. The surface epithelium of one of the two stomach samples was strongly stained by the A3 antibody.

The reactivity pattern of the A3 scfv was confirmed using the fusion protein A3 scFv-SEA(D227A). This format permitted the use of polyclonal rabbit anti-SEA antibodies for immunohistochemical detection, which is a more sensitive detection system demonstrating lower background and tissue crossreactivity as compared to the use of secondary antibodies to the peptide tag, ATPAKSE, at the C-terminus of the scFvs.

TABLE 1

Immunohistochemical reactivity to normal human tissues of soluble scFv fragments from the selected colorectal cancer phage library

| Tissue/sub-structure | n* | A3** | A10 | 3D | 1D |
|---|---|---|---|---|---|
| Esophagus | | | | | |
| /epithelial tissue | 1 | 0 | ND | ND | ND |
| /non-epithelial tissue | | 0 | ND | ND | ND |
| Colon | | | | | |
| /epithelium | 5 | ++ | + | + | ++ |
| /non-epithelial tissue | | 0 | 0 | 0 | granulocytes ++ |
| Small bowel | | | | | |
| /villi epithelium | 2 | (+) | heterogenously + | + | heterogenously (+) |
| /basal glandulae | | + | + | + | ++ |
| /non-epithelial tissue | | 0 | 0 | 0 | 0 |
| Ventricle | | | | | |
| /surface epithelium | 2 | 0, ++ | 0 | 0, + | ++ |
| /glandular epithelium | | 0 | +, ++ | 0 | ++ |
| /non-epithelial tissue | | 0 | 0 | 0 | 0 |

TABLE 1-continued

Immunohistochemical reactivity to normal human tissues of soluble scFv fragments from the selected colorectal cancer phage library

| Tissue/sub-structure | n* | A3** | A10 | 3D | 1D |
|---|---|---|---|---|---|
| Pancreas | | | | | |
| /acini | 1 | 0 | (+) | + | ++ |
| /small ducts | | (+) | (+) | + | ++ |
| /large ducts | | 0 | (+) | + | ++ |
| /non-epithelial tissue | | 0 | 0 | 0 | 0 |
| /endocrine | | 0 | 0 | 0 | 0 |
| Liver | | | | | |
| /hepatocytes | 2 | 0 | ND | ND | ND |
| /Kuppfer cells | | 0 | ND | ND | ND |
| /bile ducts | | (+) | ND | ND | ND |
| Kidney | | | | | |
| /proximal tubuli | 1 | 0 | + | 0 | luminal surface ++ |
| /distal tubuli | | 0 | + | 0 | luminal surface ++ |
| /collecting ducts | | 0 | + | 0 | luminal surface ++ |
| /glomeruli | | 0 | 0 | 0 | 0 |
| /non-epithelial tissue | | 0 | 0 | 0 | 0 |
| Bladder | | | | | |
| /epithelial tissue | 1 | 0 | ND | ND | ND |
| /non-epithelial tissue | | 0 | ND | ND | ND |
| Prostate | | | | | |
| /epithelial tissue | 1 | 0 | ++ | + | and secreted material ++ |
| /non-epithelial tissue | | 0 | 0 | 0 | 0 |
| Lung | | | | | |
| /bronchial epithelium | 1 | 0 | (+) | (+) | 0 |
| /alveolar epithelium | | 0 | (+) | (+) | 0 |
| /non-epithelial tissue | | 0 | macrophages + | macrophages + | granulocytes ++, macrophages + |
| CNS | | | | | |
| /gray matter | 1 | 0 | ND | ND | ND |
| /white matter | | 0 | ND | ND | ND |
| Skeletal muscle | 1 | 0 | ND | ND | ND |

Notes to Table 1
0 = negative, (+) = weak, + = moderate, ++ = strong, ND = not determined
*Number of tissue samples examined
**The reactivity of A3 scFv has been confirmed with the A3 scFv SEA(D227A) fusion protein

EXAMPLE 2

The A3 Tumour-Associated Antigen is Homogeneously and Frequently Expressed in Colorectal and Pancreatic Tumours The A3 scFv-SEA(D227A) fusion protein was used for immunohistochemical staining of various tumours of epithelial origin (Table 2 and FIG. 1). The fusion protein homogeneously and strongly stained 11/11 samples of primary colon cancer tissues and 4/4 metastatic colon cancer samples resected from the ovary, a lymph node and the liver. Pancreatic cancer tumours, 4/4 samples, were equally strongly positive. In contrast, tissue samples of gastric, prostate, breast and non-small cell lung carcinomas were negative.

Table 2

Tumor tissue reactivity of A3 scFv SEA(D227A)

| Tumor tissue | n | Reactivity |
|---|---|---|
| Colon cancer, primary tumors | 11 | All tumor cells are strongly and homogenously stained |
| Colon cancer metastasis in lymph node, liver and ovary | 4 | As above |
| Pancreas cancer | 4 | As above |
| Ventricle cancer | 2 | Negative |
| Prostate cancer | 2 | Negative |
| Breast cancer | 2 | Negative |
| Lung carcinoma (non-small cell) | 2 | Negative |
| Malignant melanoma | 2 | Negative |

EXAMPLE 3

The A3 TAA is Highly Expressed on the Surface of Colon Cancer Cells

The results from several Scatchard plots for affinity determination, based on the binding of the fusion proteins A3 scFv-SEA(D227A), A3 Fab and 1F scFv-SEA(D227A) (1F was classified to the A3 specificity group) to Colo205 cells, are summarised in Table 3. Specific binding was calculated by subtraction of non-specific binding to human B cell lymphoma Raji cells, a cell line not expressing the A3 and 1F TAAs, from the binding to Colo205 cells. Linear regression was used to calculate the slope and the intercept of the extrapolated line in the Scatchard plot. The A3 scFv-SEA (D227A) fusion protein saturated approximately 10-fold less binding sites per cell as compared to the A3 Fab (approx. 3 million sites per cell) fusion protein, indicating that divalent (multivalent) binding was involved for the scFv. This is supported by the more than 100-fold higher overall affinity (3.6–5.5 nM) for the A3 scFv fusion protein as compared to the A3 Fab (580–780 nM).

A single experiment performed using the 1F scFv-SEA (D227A) fusion protein, demonstrated similar binding affinity and saturation of binding sites as the A3 scFv-SEA (D227A) fusion protein.

TABLE 3

Scatchard analysis of iodinated fusion proteins binding to Colo205 cells

| Fusion protein | n* | Kd (nM) | million sites/cell |
|---|---|---|---|
| A3 Fab-SEA(D227A) | 2 | 580–780 | 3.0–3.9 |
| A3 scFv-SEA(D227A) | 3 | 3.6–5.5 | 0.11–0.39 |
| 1F scFv-SEA(D227A) | 1 | 4.2 | 0.18 |

*Number of experiments performed

EXAMPLE 4

A3 and 1F scFv-SEA(D227A) Mediate T Cell Lysis of Colo205 Cells

Figure 2:
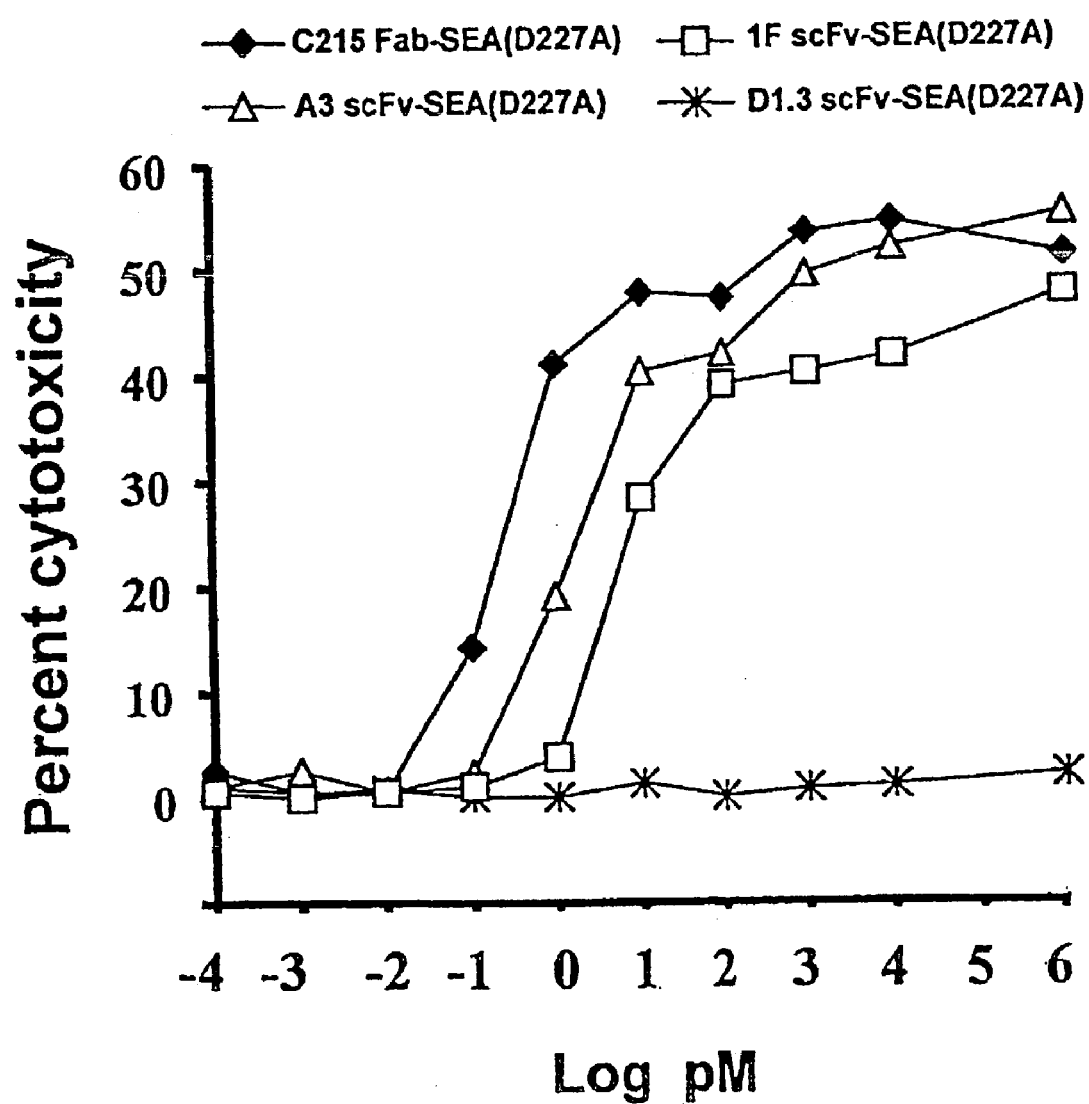

The capacity of the two fusion proteins A3 and 1F scFv-SEA(D227A) to mediate superantigen antibody dependent-cellular cytotoxicity (SADCC) towards Colo205 cells was investigated and compared with the positive control C215 Fab-SEA(D227A) and negative control D1.3 scFv-SEA(D227A) fusion proteins. The A3 scFv-SEA(D227A) fusion protein titration approached a plateau for maximal lysis which was similar, approx. 50 percent in this 4 h assay, to that demonstrated for the C215 Fab-SEA(D227A) fusion protein, although at a ten-fold higher concentration (FIG. 2). The 1F scFv-SEA(D227A) mediated a similar level of cytotoxicity at a slightly higher concentration as compared to the A3 scFv-SEA(D227A).

The negative control D1.3 scFv SEA(D227A) fusion protein did not mediate any cytotoxicity.

EXAMPLE 5

Purification of a Tumour Associated Antigen that is Recognised by the Colon Cancer Reactive Antibody A3

A tumour extract was made out of xenografted tumour cell line Colo205. The extract was applied to a pre-column coupled with C215Fab-SEAm9, and a column coupled with A3scFv-SEAm9. The columns were in series, during the application of sample but separated prior to elution under alkaline conditions.

Figure 3:
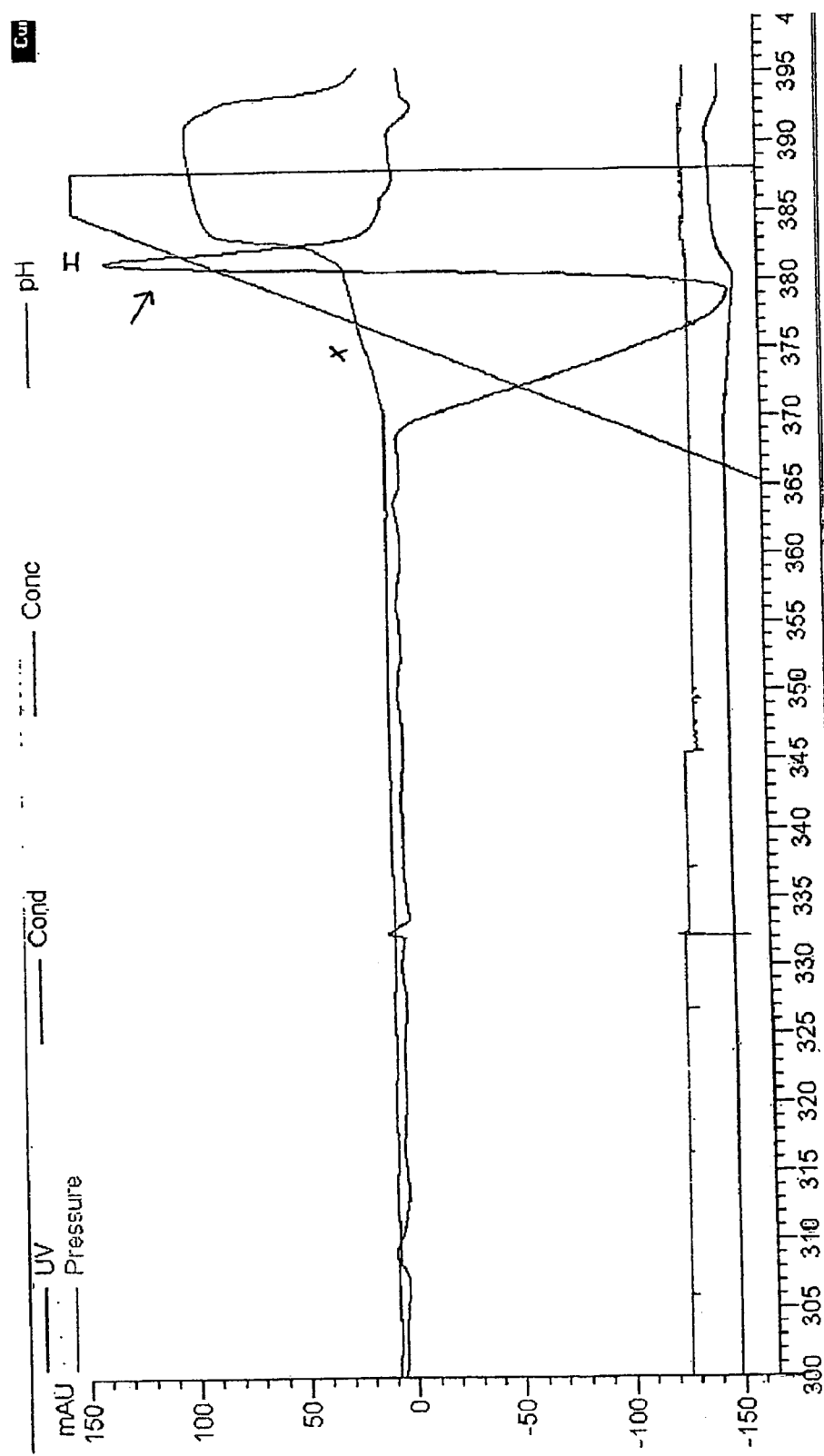
Figure 4:
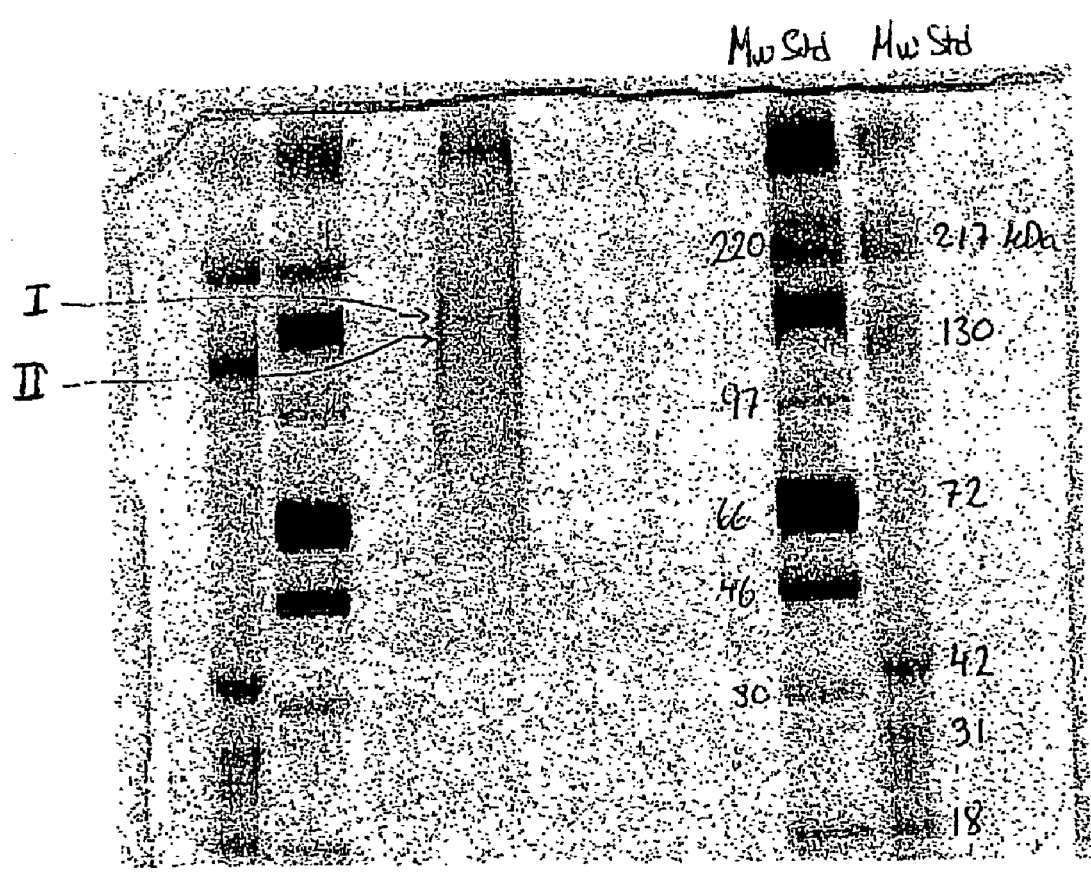

A single peak was detected during elution by UV spectroscopy (FIG. 3). This eluted fraction from the latter A3-column was collected, neutralised, concentrated, and then analysed by SDS-PAGE under non-reducing conditions (FIG. 4). Two bands visible by silver staining (labelled I and II in FIG. 4) of apparent molecular weight of approximately 90–140 kDa were cut out and examined by standard peptid mapping methodologies. These two bands corresponds to bands detected by A3 in Western Blot, see example 8. From band I 47 separate tryptic peptide masses were obtained (see SEQ ID NO: 3, Table 4, and FIG. 5 for the sequences and corresponding mass weights) which completely matched to different tryptic peptide masses. as determined by MALDI-TOF) of the human α6 integrin or β4 integrin (see SEQ ID NOs: 5–51 and 3–4, respectively, and FIGS. 3A and B, respectively, where in FIG. 3A the underlinings correspond to the peptides appearing in FIG. 3B/SEQ ID NOs: 5–51). From band II 22 separate tryptic peptide masses were obtained which completely matched to different tryptic peptide masses of β4 integrin (data not shown). The data show that the α6β4 integrin heterodimer is specifically isolated with the A3-affinity column.

TABLE 4

Peptides/polypeptides derived from human α6β4 integrin and masses thereof

| Sequence No. | Sequence | Measured Mass | Calculated Mass |
|---|---|---|---|
| 5 | LLLVGAPR | 838.568 | 838.551 |
| 6 | ANRTGGLYSCDITARGPCTR | 2226.131 | 2226.050 |
| 7 | VVTCAHRYEK | 1262.637 | 1262.631 |
| 8 | RQHVNTK | 882.524 | 882.490 |
| 9 | CYVLSQNLR | 1152.618 | 1152.583 |
| 10 | FGSCQQGVAATFTK | 1501.706 | 1501.710 |
| 11 | DFHYIVFGAPGTYNWK | 1914.881 | 1914.917 |
| 12 | DEITFVSGAPR | 1191.625 | 1191.600 |
| 13 | ANHSGAVVLLK | 1108.600 | 1108.647 |
| 14 | DGWQDIVIGAPQYFDR | 1879.865 | 1879.897 |
| 15 | DGEVGGAVYVYMNQQGR | 1842.811 | 1842.844 |
| 16 | WNNVKPIR | 1026.608 | 1026.584 |
| 17 | NIGDINQDGYPDIAVGAPYDDLGK | 2520.213 | 2520.189 |
| 18 | GISPYFGYSIAGNMDLDR | 1975.913 | 1975.922 |
| 19 | NSYPDVAVGSLSDSVTIFR | 2026.992 | 2027.008 |
| 20 | SRPVINIQK | 1054.644 | 1054.637 |
| 21 | LRPIPITASVEIQEPSSR | 1993.066 | 1993.108 |
| 22 | VNSLPEVLPILNSDEPK | 1863.920 | 1864.006 |
| 23 | TAHIDVHFLK | 1180.665 | 1180.647 |
| 24 | FSYLPIQK | 995.601 | 995.556 |
| 25 | DIALEITVTNSPSNPR | 1726.866 | 1726.897 |
| 26 | SEDEVGSLIEYEFR | 1672.764 | 1672.770 |
| 27 | VESKGLEKVTCEPQK | 1731.866 | 1731.895 |
| 28 | REITEKQIDDNRK | 1644.792 | 1644.866 |
| 29 | FSLFAER | 869.476 | 869.452 |
| 30 | YQTLNCSVNVNCVNIR | 1954.003 | 1953.927 |
| 31 | LNYLDILMR | 1150.644 | 1150.629 |
| 32 | AFIDVTAAAENIR | 1390.739 | 1390.733 |
| 33 | LPNAGTQVR | 955.523 | 955.532 |
| 34 | VSVPQTDMRPEK | 1386.727 | 1386.705 |
| 35 | EPWPNSDPPFSFK | 1547.730 | 1547.717 |
| 36 | NVISLTEDVDEFR | 1536.744 | 1536.754 |
| 37 | TQDYPSVPTLVR | 1375.718 | 1375.722 |
| 38 | RGEVGIYQVQLR | 1417.801 | 1417.791 |
| 39 | ALEHVDGTHVCQLPEDQK | 2075.965 | 2075.981 |
| 40 | GNIHLKPSFSDGLK | 1512.749 | 1512.817 |
| 41 | MDAGIICDVCTCELQK | 1928.901 | 1928.822 |
| 42 | YEGQFCEYDNFQCPR | 2012.795 | 2012.790 |
| 43 | SCVQCQAWGTGEKKGR | 1879.865 | 1879.890 |

TABLE 4-continued

Peptides/polypeptides derived from human α6β4 integrin and masses thereof

| Sequence No. | Sequence | Measured Mass | Calculated Mass |
|---|---|---|---|
| 44 | DEDDDCTYSYTMEGDGAPGPNSTVLVHK | 3103.229 | 3103.278 |
| 45 | QEVEENLNEVYR | 1521.779 | 1521.718 |
| 46 | VAPGYYTLTADQDAR | 1640.779 | 1640.791 |
| 47 | VPLFIRPEDDDEK | 1572.778 | 1572.790 |
| 48 | DVVSFEQPEFSVSR | 1625.758 | 1625.781 |
| 49 | LLELQEVDSLLR | 1427.760 | 1427.810 |
| 50 | VCAYGAQGEGPYSSLVSCR | 2060.883 | 2060.916 |
| 51 | VLVDNPKNR | 1054.644 | 1054.600 |

Materials and Methods.

Solubilisation of Tumour Tissue

Human colon cancer tissue expressing the A3 antigen was provided by hospitals in Sweden and stored frozen at −70° C. in the tissue bank at ABR. Frozen colon cancer tissues were sliced with a scalpel and transferred into a tube containing cold isotonic sucrose buffer (0.25M sucrose, 10 mM KCl, 1.5M $MgCl_2$, 50 mM Tris-HCl pH 7.4 at 25° C.) containing 1% (v/v) Nonidet P-40 (NP-40) and protease inhibitors (Completet™ Protease Inhibitor Cocktail Tablet, Boehringer Mannheim). Tissue was homogenised with an Ultra-Turrax homogeniser and were left to solubilise at 0° C. The solubilised preparation was centrifuged at 11,000 rpm (Hettich centrifuge Universal 30 RF rotor), to remove cell debris. The supernatant was further centrifuged at 108,000 g at 4° C. (Beckman Ultracentrifuge Ti-60 rotor), and finally filtered through a 0.2 μm Minisart plus filter (Sartoriuis AG Gottingen Germany).

Affinity Purification of Tissue Antigens

A3scFv-SEAm9 was coupled to a NHS-activated HiTrap® column (Pharmacia Biotech Uppsala Sweden), according to the manufacturer's recommendations. The control and pre-column were coupled with C215Fab-SEAm9, and the control, pre-column and column were set up in series. All columns were washed with pre-wash buffer (20 mM Tris HCl pH7.5 at 4° C. containing 0.2% NP 40). The extract was loaded onto the column at 0.1 ml/min, and the flow through was recirculated. The columns were then washed with start buffer. Bound antigen was eluted in a pH gradient of diethylamine starting at pH 7.5 up to 11.0. 2.5 ml of eluant was collected and concentrated down to 75 μl. The purification was performed at 4° C. using an AKTA FPLC system (Amersham Pharmacia Biotech Uppsala Sweden) Eluted protein was analysed by SDS PAGE and silver staining. Individual bands were excised, digested with trypsin and the masses of the peptide were determined using a MALDI-TOF instrument by Protana A/S (Odense, Denmark). The peptide masses were then compared in a computer search with all tryptic peptide masses for each protein in the SWISSPROT database, a service provided by Protana A/S (Odense Denmark).

EXAMPLE 6

A3scFv-SEAm9 Detects a Novel α6β4 Integrin Epitope

Figure 6:
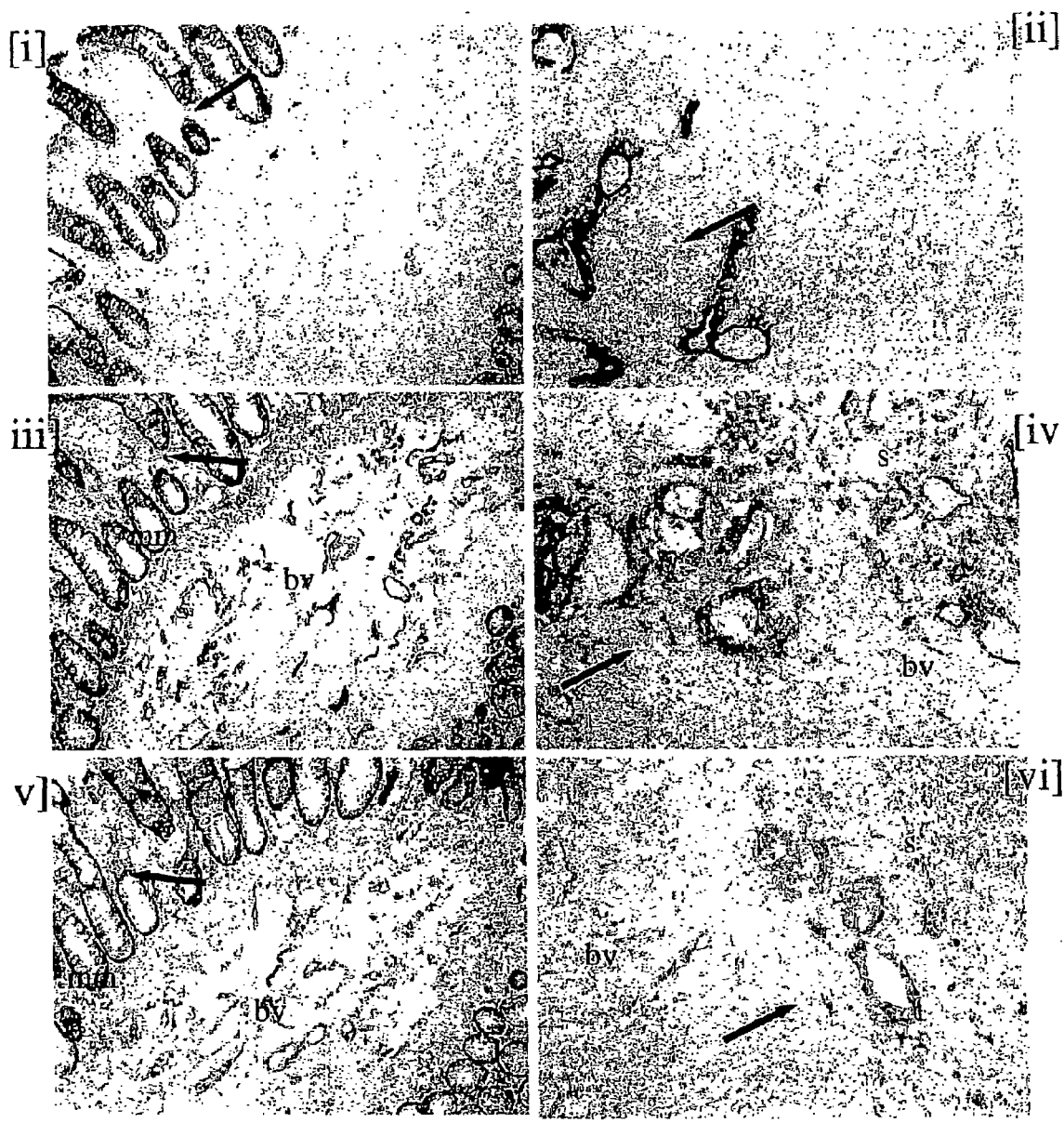

Commercial antibodies to human α6 integrin and β4 integrin were compared to A3 on normal and malignant colon sections. The reactivity, shown in FIG. 6, demonstrates that A3 is restricted to the colon epithelium (FIG. 6 [i]), and malignant cell in the tumour (FIG. 6 [ii]). Commercial antibody NKI-GoH3 to α6 integrin, also reacted with normal colon (FIG. 6 [iii]) and colon cancer (FIG. 6 [iv]). Reaction was seen in epithelial cells of colon and malignant cells (arrows) but also in blood vessels (BV), some stromal components (s) and in muscularis mucosae (mm). The reaction observed with commercial ASC-3 anti-β4 integrin antibody was similar to that noted with anti-α6 antibody but weaker, in both normal colon (v) and colon cancer (vi).

Materials and Methods

Antibody

A3 scFv was selected from the *M fascicularis* library. The VH and VL genes from this were released by restriction enzyme digestion and fused to the Staphylococcal Enterotoxin AE chimeric mutant (D227A) to generate the A3scFv-SEAm9. This demonstrated very low levels of non-specific binding and allowed sensitive detection by secondary antibodies. ASC-3 anti-human-β4 integrin antibody and NKI-GoH3 anti-human-α6 integrin antibody were from Becton Dickinson (Copenhagen, Denmark)

Immunohistochemistry

Tumour and normal tissue samples were obtained from the Department of Surgery Lund Hospital. These were rate-frozen in iso-pentane, which had been pre-cooled in liquid nitrogen. Samples were stored at −70° C. until sectioned. After cryosectioning the sections were air dried over night, fixed in cold acetone and blocked with avidin/biotin (Vector Burlingame Calif.). Primary antibody was then added to the section for one hour.

The secondary antibodies were incubated for 30 minutes followed by streptavidin-biotin/HRP (Dakopatts Copenhagen Denmark) for a further 30 minutes. Extensive washing was perfromed between all these steps with 50 mM Tris pH 7.6, 0.15M NaCl. Diaminobenzidine (DAB) was used as chromogen and the sections were counterstained in 0.5% methyl green. Controls included a non-tissue reactive Fab and SEA-D227A or no primary antibody. All antibodies were used at a final concentration of 5 μg/ml. Results were expressed as negative, weak, moderate or strong staining.

EXAMPLE 7

Figure 7A:
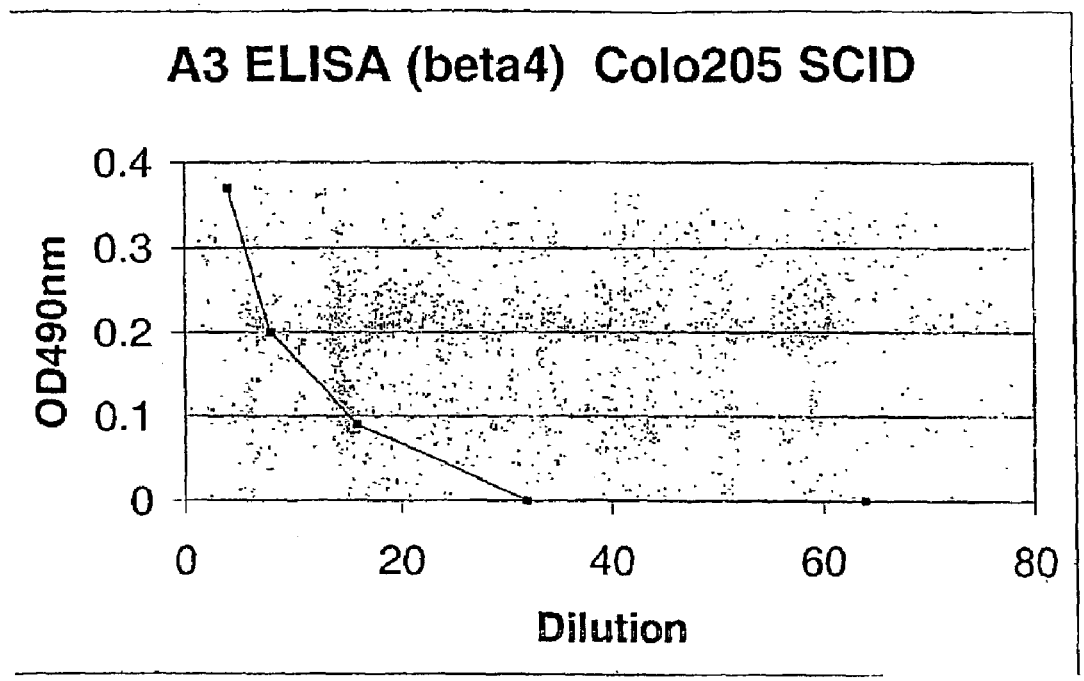
Figure 7B:
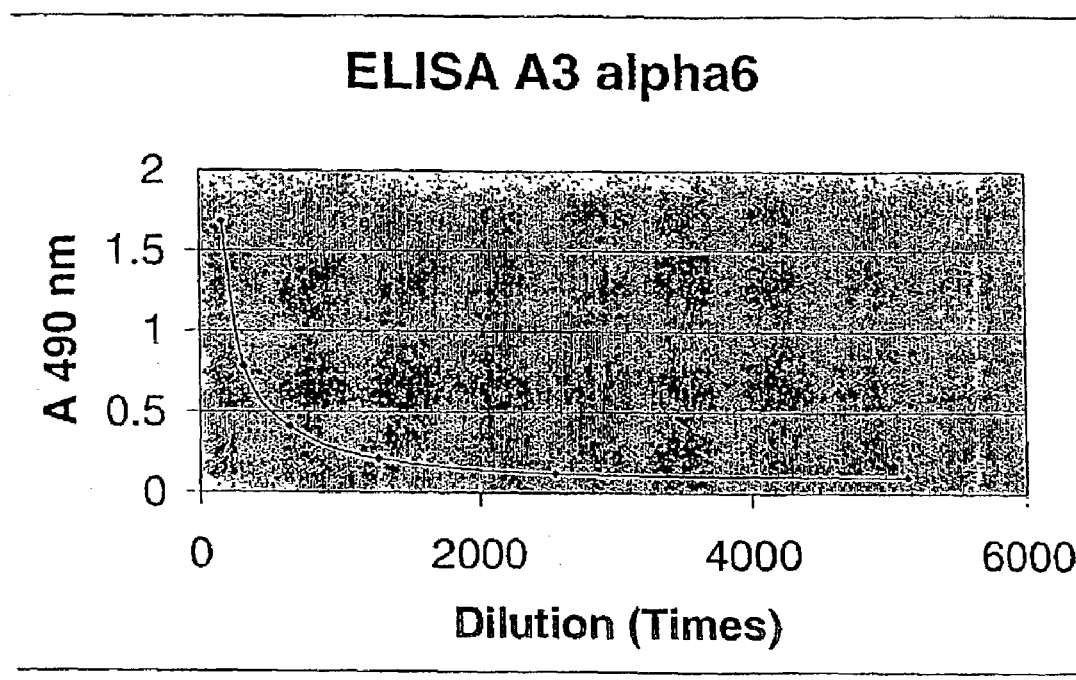

The A3 Tumour Associated Antigen Reacted with α6 and β64 Integrin Antibodies in a Capture ELISA Crude tumor extract or A3 antigen purified by A3-affinity chromatography (see example 5) was analysed by a capture ELISA. Commercial antibody ASC-3 specific for beta 4 integrin were used as capture antibody, to which different dilutions of crude tumor extract was applied. This was then chased with A3scFv-SEAm9. Bound A3scFv-SEAm9 was then detected with anti-SEA-HRP (FIG. 7A). In FIG. 7B the commercial anti-α6 integrin antibody NKI-GoH3 was used to capture different dilutions of the concentrated A3-affinity purified eluate. In a similar way as in FIG. 7A the captured proteins were chased with A3scFv-SEAm9 and detected with anti-SEA-HRP. In both experiments a concentration dependent signal was detected. These results confirm the specificity of A3 to α6β4 intergin heterodimer, which was also shown to be specifically isolated from the A3-affinity column in example 5.

Material and Methods

Commercial antibodies NKI-GoH3 or ASC-3 (Becton Dickinson Copenhagen Denmark) 100 μl, were used to coat the well of an E.I.A./R.I.A.-plate (Costar) in 0.05 M NaHCO3, pH 9.6. The reaction was allowed to continue overnight at 4° C., after which the plates were washed 4 times in DPBS+0.05% Tween 20. Wells were then blocked with 200 μl 3% non-fat milk powder in DPBS+0.05% Tween 20, for 1–2 h at room temperature (RT) with shaking. Wells were again washed as above and 100 μl antigen extract diluted in 3% non-fat milk powder in DPBS+0.05% Tween 20, was applied for 2 h at RT with shaking. Wells were again washed (4×DPBS+0.05% Tween 20) after which 100 μl of the primary antibody diluted in 3% non-fat milk powder in DPBS+0.05% Tween 20 was incuabted for 2 h at RT with shaking. Wells were washed again as above and 100 μl of the secondary antibody diluted in 3% non-fat milkpowder in DPBS+0.05% Tween 20 was added to each well for 1 h at RT with shaking. Wells were again washed as above and colour developed by the addition of 100 μl peroxidase substrate (Sigma Fast OPD Peroxidase Substrate Tablet Set P-9187). The reaction was allowed to continue for 30 min at RT, in the dark and shaking before the reaction was stopped by the addition of 50 μl 3 M $H_2SO_4$. The absorbance was read at 490 nm.

EXAMPLE 8

Western Blot Analysis of the A3 Tumour Antigen

A3-affinity purified tumour antigen extracts were separated by SDS-PAGE and transferred to membranes for Western blot analysis. Extracts were applied directly or heated to 100° C. for 5 minutes or heated to 100° C. for 5 minutes but in the presence of mercaptoethanol (BME) (FIG. 8). The membranes were then probed with A3scFv-SEAm9 and anti-SEA-HRP or anti-human-α6 integrin or anti-human-β4 integrin antibodies. The anti-β4 integrin antibody did not react with any protein on the membrane (FIG. 8 [ii]). The anti-human-α6 integrin reacted with a major specie with apparent molecular weight between 90–140 kDa in the A3-affinity purified tumour antigen extract (FIG. 8 [iii]). The same species was also detected by A3scFv-SEAm9, which also was detected after heating but was much weaker under reduced conditions (with BME present) (FIG. 8 [i]). The major band detected in the 90–140 kDa interval corresponds to the bands in example 5, that were analysed by peptide mapping and were found to contain α6 integrin and β4 integrin.

Materials and Methods

ASC-3 anti-human-β4 integrin antibody and NKI-GoH3 anti-human-α6 integrin antibody were from Becton Dickinson (Copenhagen, Denmark). Samples were resolved by SDS-PAGE in 0.25M tris-glycine pH 8.9 and 0.1% SDS at 100V through the upper gel, then 170V through the resolving gel. Molecular weight standards (Biorad broad Range, Biorad) were included on all gels. Resolved samples were transferred to nitrocellulose (Biorad) in transfer buffer (10 mM Tris base, 2M glycine, 40% (v/v) methanol) at 100V for 1 hour. Membranes were blocked with 5% (w/v) BSA/TBS for at least 2 hours at 4° C., then incubated with the appropriate antibody diluted in 5% BSA/TBS/0.2% azide. This reaction was allowed to proceed for at least 2 hours at RT, after which the membrane was washed extensively in TBST-T. Bound antibody was detected by incubation of membranes for 1 hour with HRP conjugated antibody diluted in TSB-T containing 5% milk powder. Membranes were then incubated with enhanced chemiluminescence (ECL) detection reagents (Renaissance® NEN™ Life Science Products, Boston Mass.) for 1 minute and exposed to film for up to 1 hour.

REFERENCES

1. DeCosse J J, Tsioulias G J, Jacobson J S. Colorectal cancer: detection, treatment, and rehabilitation. *CA Cancer J Clin* 1994; 44: 27–42.
2. Riethmuller G, et al. Monoclonal antibody therapy for resected Dukes' C colorectal cancer: seven-year outcome of a multicenter randomized trial. *J Clin Oncol* 1998; 16: 1788–1794.
3. Kuhn J A, Thomas G. Monoclonal antibodies and colorectal carcinoma: a clinical review of diagnostic applications. *Cancer Invest* 1994; 12: 314–323.
4. Tordsson J, et al. Efficient selection of scfv antibody phage by adsorption to in situ expressed antigens in tissue sections. *J Immunol Methods* 1997; 210: 11–23.
5. Aujame L, Geoffroy F, Sodoyer R. High affinity human antibodies by phage display. *Hum Antibodies* 1997; 8: 155–168.
6. Clark R K, Trainer D L, Bailey D S, Greig R G Immunohistochemical analysis of antiserum from rhesus monkeys immunized with human colon carcinoma. *Cancer Res* 1989; 49: 3656–3661.
7. Lewis A P, et al. Cloning and sequence analysis of kappa and gamma cynomolgus monkey immunoglobulin cDNAs. *Dev Comp Immunol* 1993; 17: 549–560.
8. Brodin T N, et al. Man-made superantigens: Tumor-selective agents for T-cell-based therapy. *Adv Drug Deliv Rev* 1998; 31: 131–142.
9. Dohlsten M, et al. Monoclonal antibody-superantigen fusion proteins: tumor-specific agents for T-cell-based tumor therapy. *Proc Natl Acad Sci USA* 1994; 91: 8945–8949.
10. Liu C, et al. Eradication of large colon tumor xenografts by targeted delivery of maytansinoids. *Proc Natl Acad Sci USA* 1996; 93: 8618–8623.

LEGENDS TO FIGURES

FIG. 1 The A3 Tumour-Associated Antigen is Homogeneously Expressed in Primary and Metastatic Tumours Immunohistochemical staining of frozen and acetone fixed sections of human tumour tissues using A3 scFv-SEA (D227A) and C215 Fab-SEA(D227A) at 70 nM. The A3 scFv fusion protein reacted strongly and homogeneously with both primary colon and pancreatic carcinoma resected from tumour patients. A representative staining of a primary colon cancer is shown for C215 Fab-SEA(D227A) in (A) and for A3 scFv-SEA(D227A) in (B). Staining by A3 scFv-SEA(D227A) of a colon cancer liver metastasis is shown in (C) and of a primary pancreatic cancer in (D).

FIG. 2 A3 scFv-SEA(D227A) Coated Colo205 Tumour Cells are Efficiently Killed by T Cells.

Superantigen antibody dependent cellular cytotoxicity (SADCC) towards Colo205 cells mediated by A3 scFv-SEA (D227A) reached the same maximal cytotoxicity as the anti-Ep-CAM fusion protein C215 Fab-SEA(D227A), although at a ten-fold higher concentration. The absence of cytotoxicity mediated by the D1.3 scFv-SEA(D227A) demonstrates the need of a tumour targeting antibody moiety in the fusion protein.

FIG. 3

Immunoaffinity chromatography of tumor extract on a A3scFv-SEAm9 coupled column. Protein bound to A3 coupled columns was washed extensively then eluted as described in Materials and Methods in Example 5. The eluted fractions were examined by UV spectroscopy (arrow) and a single peak identified. The sample was eluted with a pH gradient as indicated by an x.

FIG. 4

A3 antigen preparation was separated on a non-reduced SDS PAGE and silver-stained. Previous Western analysis had defined a molecular weight range in which the A3 antigen was believed to reside. The bands evident within this region (Labelled I and II) were excised for peptide mapping analysis FIGS. 5A and 5B Epithelial integrin α6β4: complete primary structure of α6 and variant forms of β4 (precursor) (Tamura et al J Cell Biol 111:1593–1604 (1990)). The matched peptides shown in SEQ ID NOs: 5–51 are underlined in the sequences of human α6 (FIG. 5A) integrin and β4 (precursor) (FIG. 5B) integrin as published.

FIG. 6

Immunohistochemistry of normal and malignant colon using A3scFv and commercial anti-human α6 and β4 integrin monoclonal antibodies.

FIGS. 7A and 7B

Capture ELISA. In FIG. 7A monoclonal antibody ASC-3 specific for β4 integrin was used as capture antibody, to which different dilutions of crude tumor extract was applied. In FIG. 7B the anti-α6 integrin monoclonal anti-body NKI-GoH3 was used to capture different dilutions of the concentrated A3-affinity purified eluate. In both FIGS. 7A and 7B the captured integrin antigen was then successfully detected with A3scFv-SEAm9.

Figure 8A:
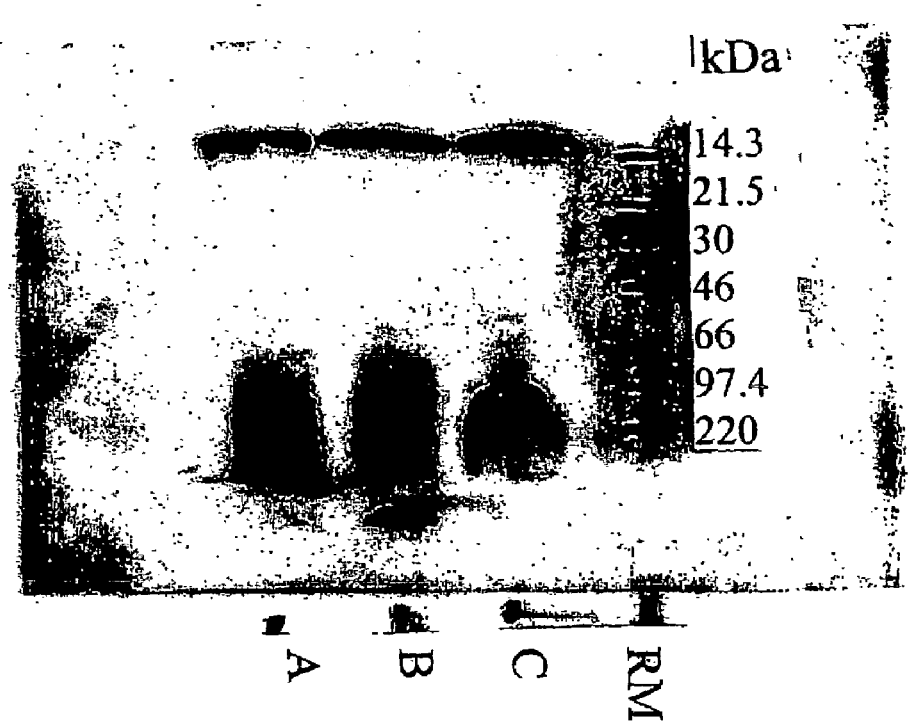
Figure 8B:
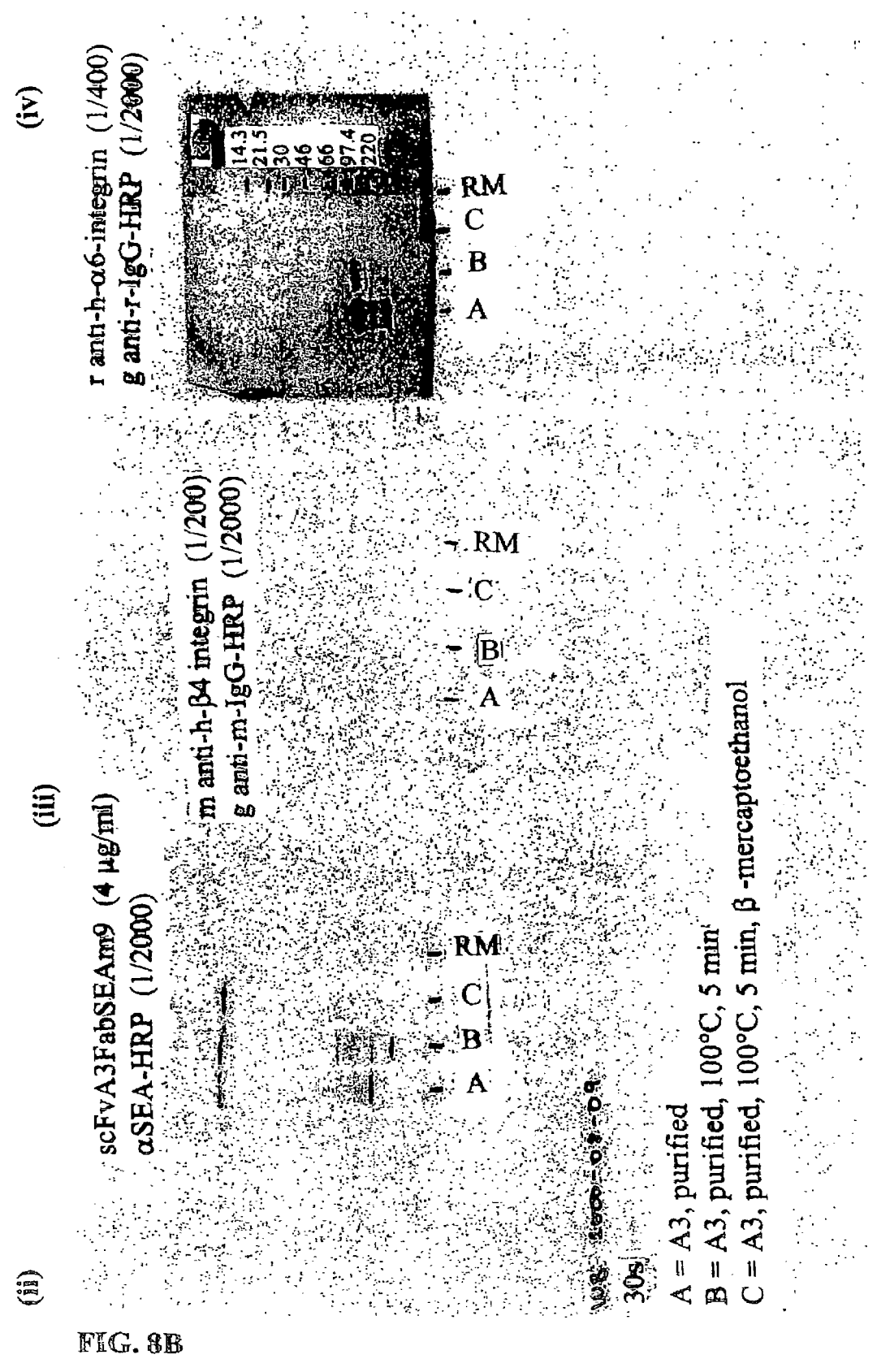

FIGS. 8A and 8B

Western blot analysis of the eluate from the A3-affinity column. The primary antibodies used are (i) and (ii) A3scFv-SEAm9, (iii) ASC-3 anti-human-β4 integrin antibody and (iv) NKI-GoH3 anti-human-α6 integrin anti-body. Lane A—the eluate was applied directly, lane B—the eluate was heated to 100° C. for 5 minutes, and lane C—the eluate was heated to 100° C. for 5 minutes but in the presence of mercaptoethanol. Positions of molecular weight standards are indicated.

The invention claimed is:

1. An isolated antibody, or a fragment thereof, having a binding structure for a target structure displayed in, and on the cell surface of, human gastrointestinal epithelial tumour cells, said binding structure comprising the complementarity determining region (CDR) sequences in the light chain comprising essentially the amino acids number 23–33 (CDR1), 49–55 (CDR2), 88–98 (CDR3) of the amino acid sequence shown in SEQ ID NO:2, and the CDR sequences in the heavy chain comprising essentially the amino acids number 158–162 (CDR1), 177–193 (CDR2), 226–238 (CDR3) of the amino acid sequence shown in SEQ ID NO:2.

2. An isolated antibody according to claim 1, wherein the sequences are of *Macaca fascicularis* origin.

3. An isolated antibody or fragment thereof according to claim 1, wherein the sequences of the antibody or fragment thereof have complimentary determining region (CDR) sequences according to claim 1,
and wherein the sequences of the antibody or fragment thereof have an identity of at least 84% to corresponding sequences of human origin which are not said complementary determining region (CDR) sequences.

4. An isolated antibody according to claim 1, which has low immunogenicity or non-immunogenicity in humans.

5. An isolated antibody according to claim 1, which has been derivatised by genetically linking to other polypeptides, and/or by chemical conjugation to organic or non-organic chemical molecules, and/or by di-, oligo- or multi-merisation.

6. An isolated antibody according to claim 1, which is genetically linked or chemically conjugated to cytotoxic polypeptides or to cytotoxic organic or non-organic chemical molecules.

7. An isolated antibody according to claim 1, which is genetically linked or chemically conjugated to biologically active molecules.

8. An isolated antibody according to claim 1, which is genetically linked or chemically conjugated to immune activating molecules.

9. An isolated antibody according to claim 1, which is labeled and the binding thereof is inhibited by an unlabeled form of said antibody.

10. An isolated antibody according to claim 1, wherein said binding structure recognizes a non-reduced form of α6β4 integrin.

* * * * *